US012127828B2

(12) United States Patent
Auerbach et al.

(10) Patent No.: US 12,127,828 B2
(45) Date of Patent: Oct. 29, 2024

(54) MONITORING SYSTEM

(71) Applicant: BreatheVision Ltd., Hof Ashkelon (IL)

(72) Inventors: Ditza Auerbach, Aseret (IL); Menashe Terem, Yavne (IL)

(73) Assignee: BreatheVision Ltd., Nes Ziona (IL)

( * ) Notice: Subject to any disclaimer, the term of this patent is extended or adjusted under 35 U.S.C. 154(b) by 360 days.

(21) Appl. No.: 16/644,561

(22) PCT Filed: Sep. 5, 2018

(86) PCT No.: PCT/IL2018/050992
§ 371 (c)(1),
(2) Date: Mar. 5, 2020

(87) PCT Pub. No.: WO2019/049137
PCT Pub. Date: Mar. 14, 2019

(65) Prior Publication Data
US 2020/0260998 A1   Aug. 20, 2020

Related U.S. Application Data

(60) Provisional application No. 62/674,079, filed on May 21, 2018, provisional application No. 62/624,247, (Continued)

(51) Int. Cl.
*A61B 5/113* (2006.01)
*A61B 5/00* (2006.01)
(Continued)

(52) U.S. Cl.
CPC .......... *A61B 5/1135* (2013.01); *A61B 5/0064* (2013.01); *A61B 5/05* (2013.01);
(Continued)

(58) Field of Classification Search
CPC .... A61B 2562/0219; A61B 2562/0223; A61B 5/1135; A61B 5/6804; A61B 5/6833
See application file for complete search history.

(56) References Cited

U.S. PATENT DOCUMENTS 5,825,293 A   10/1998  Ahmed et al.
6,351,662 B1   2/2002  Franck et al.
(Continued)

FOREIGN PATENT DOCUMENTS

CN      206470692      9/2017
WO     WO 99/65434    12/1999
(Continued)

OTHER PUBLICATIONS

Aliverti A. Physiology masterclass: The respiratory muscles during exercise. Breathe 2016; 12: 165-168. (Year: 2016).*
(Continued)

*Primary Examiner* — Yi-Shan Yang

(57) ABSTRACT

A wearable motion monitoring device including: a housing sized and shaped to be positioned between a body region of a subject and a garment worn by the subject; a marker included in the housing, the marker including at least one light emitter, wherein the light emitter is positioned to emit light from an upper surface of the marker, such that the at least one light emitter is indicative of displacements of the body region; and at least one garment holder incorporated in the housing, wherein the holder serves as an anchoring point between the marker and the garment, the garment overlying the marker when anchored by the at least one garment holder.

18 Claims, 28 Drawing Sheets

Related U.S. Application Data filed on Jan. 31, 2018, provisional application No. 62/554,250, filed on Sep. 5, 2017.

(51) Int. Cl.
*A61B 5/05* (2021.01)
*A61B 5/11* (2006.01)

(52) U.S. Cl.
CPC .......... *A61B 5/1127* (2013.01); *A61B 5/4818* (2013.01); *A61B 5/6833* (2013.01); *A61B 2503/04* (2013.01); *A61B 2562/0219* (2013.01); *A61B 2562/0223* (2013.01)

(56) References Cited

U.S. PATENT DOCUMENTS

| | | |
|---|---|---|
| 6,352,517 B1 | 3/2002 | Flock et al. |
| D487,173 S | 2/2004 | Clare et al. |
| 6,937,696 B1 | 8/2005 | Mostafavi |
| 8,527,217 B2 | 9/2013 | Moodie |
| 8,790,274 B2 | 7/2014 | McCool |
| 2002/0188194 A1 | 12/2002 | Cosman |
| 2003/0100843 A1 | 5/2003 | Hoffman |
| 2005/0201509 A1 | 9/2005 | Mostafavi et al. |
| 2007/0016009 A1 | 1/2007 | Lakin et al. |
| 2007/0039214 A1 | 2/2007 | Schmidt |
| 2007/0293781 A1 | 12/2007 | Sims et al. |
| 2008/0287728 A1 | 11/2008 | Mostafavi et al. |
| 2008/0287769 A1 | 11/2008 | Kurzweil et al. |
| 2009/0305212 A1 | 12/2009 | McKenzie et al. |
| 2010/0183196 A1 | 7/2010 | Fu et al. |
| 2011/0015521 A1 | 1/2011 | Faul |
| 2011/0144517 A1 | 6/2011 | Cervantes |
| 2012/0165645 A1 | 6/2012 | Russell et al. |
| 2012/0232431 A1 | 9/2012 | Hudson |
| 2013/0018232 A1 | 1/2013 | D'Souza et al. |
| 2013/0030257 A1 | 1/2013 | Nakata et al. |
| 2014/0051946 A1 | 2/2014 | Arne et al. |
| 2014/0228657 A1 | 8/2014 | Palley et al. |
| 2015/0087922 A1* | 3/2015 | Bardy ............... A61B 5/0006 600/301 |
| 2016/0029949 A1* | 2/2016 | Landesberg ......... A61B 5/7278 600/534 |
| 2016/0235344 A1 | 8/2016 | Auerbach |
| 2017/0055896 A1* | 3/2017 | Al-Ali ............... A61B 5/6823 |
| 2017/0196513 A1* | 7/2017 | Longinotti-Buitoni ............... A61B 5/7405 |
| 2018/0235537 A1* | 8/2018 | Whiting ............... A61N 1/3621 |
| 2019/0290799 A1* | 9/2019 | Arshi ............... A61L 15/42 |

FOREIGN PATENT DOCUMENTS

| | | |
|---|---|---|
| WO | WO 01/76467 | 10/2001 |
| WO | WO 02/30279 | 4/2002 |
| WO | WO 2004/049109 | 6/2004 |
| WO | WO 2006/005021 | 1/2006 |
| WO | WO 2009/011643 | 1/2009 |
| WO | WO 2015/062969 | 5/2015 |
| WO | WO 2019/049137 | 3/2019 |

OTHER PUBLICATIONS

Yoon et al., "Improvement of dynamic respiration monitoring through sensor fusion of accelerometer and gyro-sensor". J. of Electr Eng Technol. 2014, vol. 9, No. 1: 334-343 (Year: 2014).*

Supplementary European Search Report and the European Search Opinion Dated Apr. 19, 2021 From the European Patent Office Re. Application No. 18853012.5. (14 Pages).

Chan et al. "Wireless Patch Sensor for Rmote Monitoring of Heart Rate, Respiration, Activity, and Falls", 2013 34th Annual International Conference of the IEEE EMBS, Engineering in Medicine and Biology Society, XP032488906, Osaka, Japan, Jul. 3-7, 2013, p. 6115-6118, Jul. 3, 2013.

International Preliminary Report on Patentability Dated Mar. 19, 2020 From the International Bureau of WIPO Re. Application No. PCT/IL2018/050992. (10 Pages).

International Search Report and the Written Opinion Dated Dec. 31, 2018 From the International Searching Authority Re. Application No. PCT/IL2018/050992. (16 Pages).

Ernst et al. "Correlation Between External and Internal Respiratory Motion: A Validation Study", International Journal of Computer Assisted Radiology and Surgery, CARS, 7(3): 483-492, Published Online Aug. 19, 2011.

McClelland et al. "Respiratory Motion Models: A Review", Medical Image Analysis, 17(1): 19-42, Available Online Oct. 8, 2012.

Communication Pursuant to Article 94(3) EPC Dated Aug. 22, 2023 From the European Patent Office Re. Application No. 18853012.5 (9 Pages).

* cited by examiner

Fig 8A
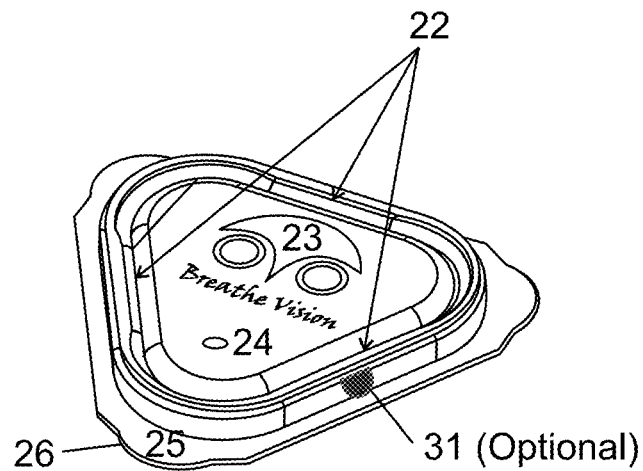
Exemplary clothing (i)
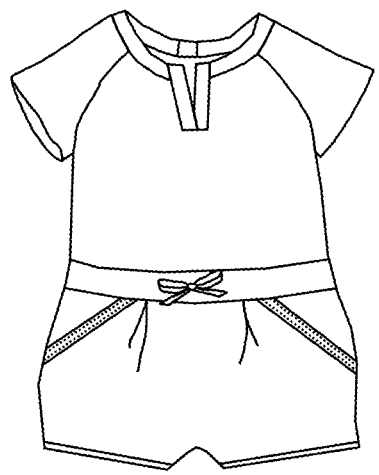
Exemplary pouch (ii)
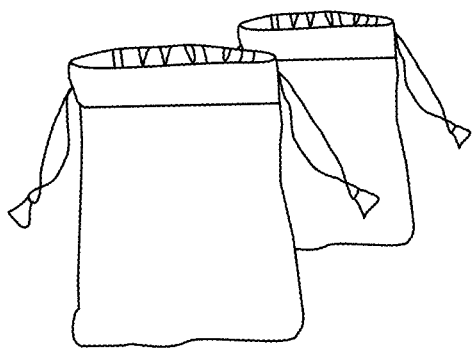

1200

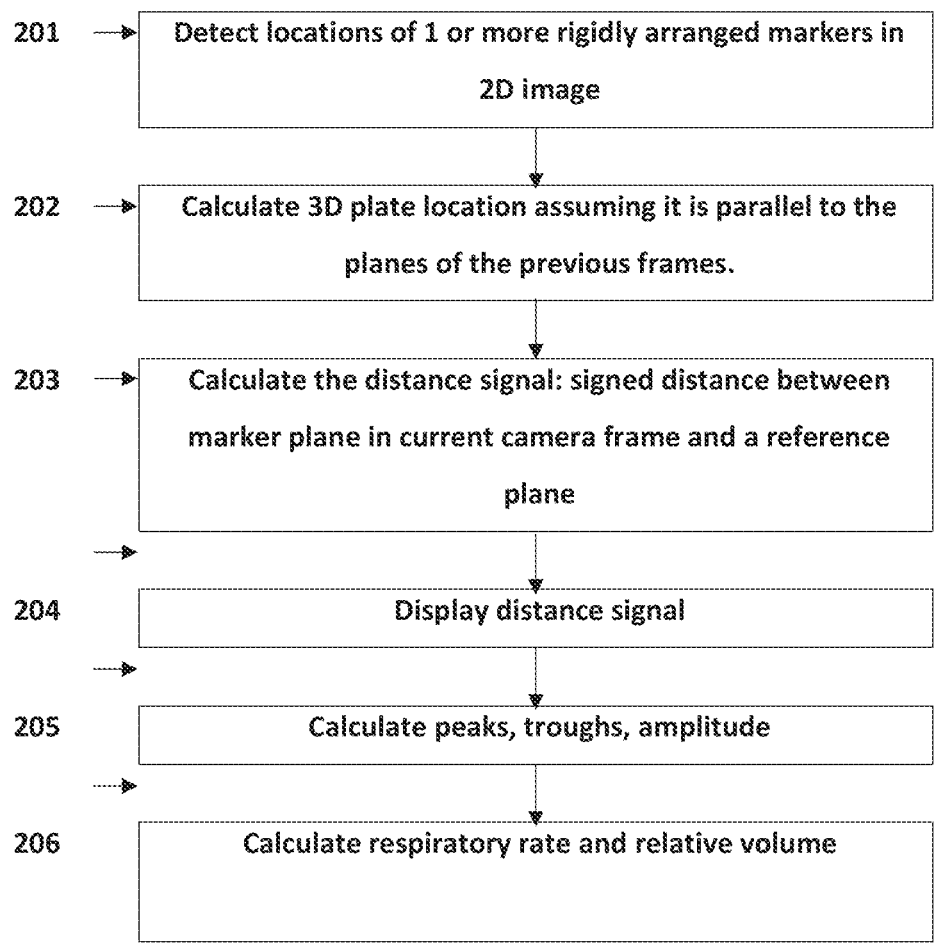

1600

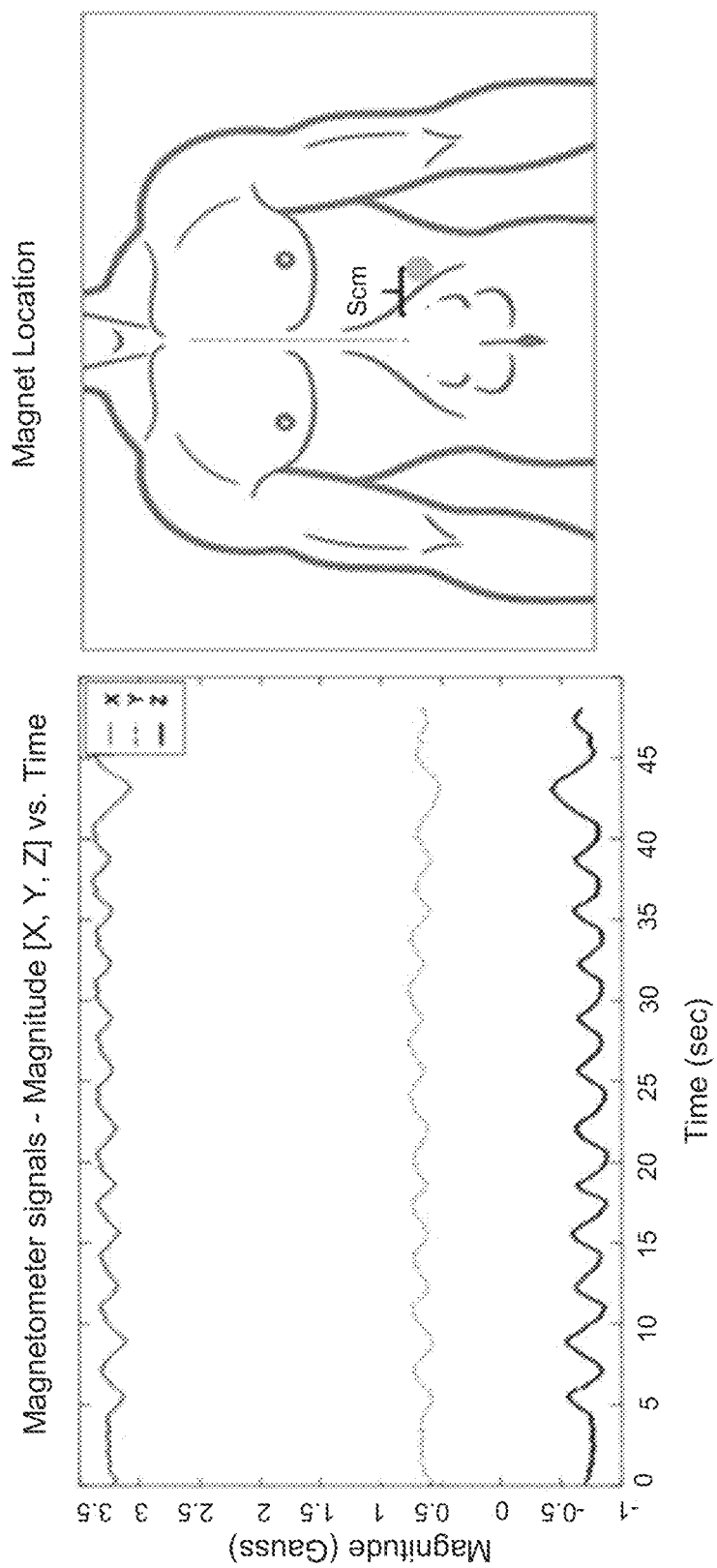

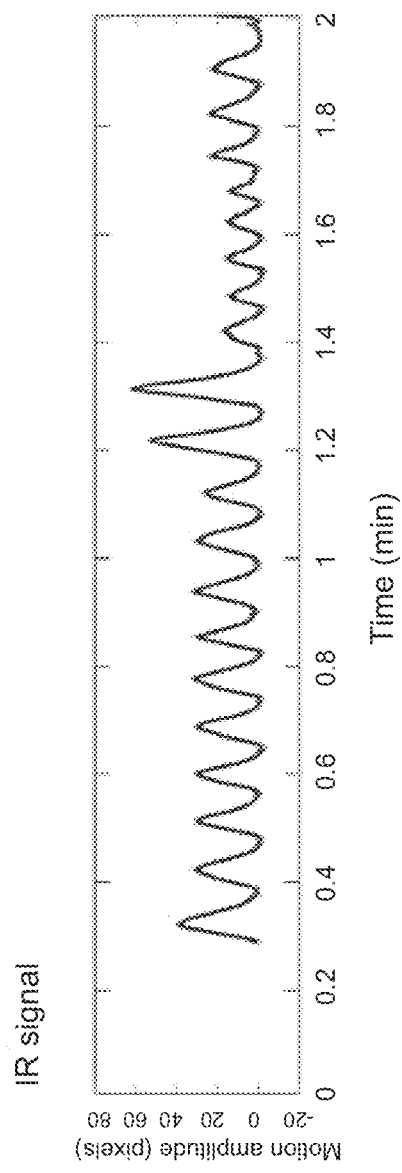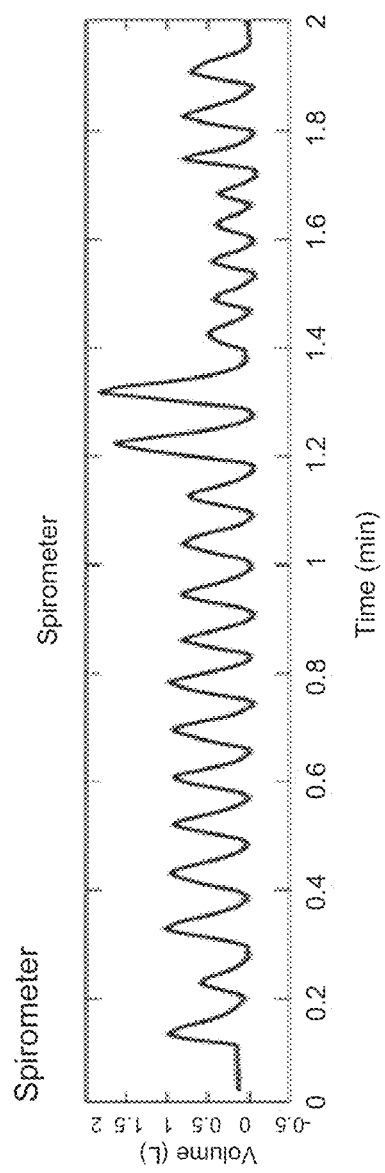

MONITORING SYSTEM

RELATED APPLICATIONS

This application is a National Phase of PCT Patent Application No. PCT/IL2018/050992 having International filing date of Sep. 5, 2018, which claims the benefit of priority under 35 USC § 119(e) of U.S. Provisional Patent Application Nos. 62/674,079, filed on May 21 2018; 62/624,247, filed on Jan. 31, 2018 and 62/554,250, filed on Sep. 5, 2017. The contents of the above applications are all incorporated by reference as if fully set forth herein in their entirety.

FIELD AND BACKGROUND OF THE INVENTION

The present invention, in some embodiments thereof, relates to monitoring apparatus, methods and systems. More particularly, some embodiments relate to a wearable device for monitoring motion which is related to physiological characteristics; in particular, those related to vital signs and breathing parameters.

Movement of various parts of the body can be tracked in order to deduce various physiological characteristics.

Background art includes U.S. Patent No. US2016/0235344A1 that describes "A system for monitoring the respiratory activity of a subject, which comprises one or more signal generating elements being kinematic or light emitting elements, applied to the thorax of a subject, for generating signals that are indicative of movement of the thorax of the subject; a receiver for receiving the generated signals during breathing motion of the subject; and one or more computing devices in data communication with the receiver, for analyzing the breathing motion.

The more computing device is operable to calculate, in response to the received generated signals, the magnitude of a maximum displacement in 3D space of the one or more signal generating elements during a cycle of the breathing motion; and to calculate the magnitude of a current displacement in 3D space of the one or more signal generating elements during the breathing motion with respect to a reference tidal volume associated with the maximum displacement in 3D space."

U.S. Patent No. US9788762B2 that describes "A system for monitoring the respiratory activity of a subject, which comprises one or more signal generating elements being kinematic or light emitting elements, applied to the thorax of a subject, for generating signals that are indicative of movement of the thorax of the subject; a receiver for receiving the generated signals during breathing motion of the subject; and one or more computing devices in data communication with the receiver, for analyzing the breathing motion.

The more computing device is operable to calculate, in response to the received generated signals, the magnitude of a maximum displacement in 3D space of the one or more signal generating elements during a cycle of the breathing motion; and to calculate the magnitude of a current displacement in 3D space of the one or more signal generating elements during the breathing motion with respect to a reference tidal volume associated with the maximum displacement in 3D space."

U.S. Design Patent No. US D487,173 S that describes a "gripper".

U.S. Patent No. US2007/0039214 A1 that describes "an apparatus for uniformly pulling a base fabric taut for rug hooking. The apparatus includes an open rectangular frame having spaced parallel upper and lower members and spaced parallel side members having upper surfaces in a common plane. Grippers are pivotally supported on each of the frame members, wherein each of the grippers has a hinged outer edge and an upper surface adapted to grip the base fabric. Each gripper is independently pivotal between a relaxed position wherein the upper surface is parallel to the frame common plane and a raised position in which its upper surface is inclined outwardly. The apparatus further includes gripper actuators each having a gripper engagement end and a hand engagement end. The actuators are pivotal between a relaxed position and an engaged position, whereby the actuator moves the gripper to its raised position when the actuator is moved to the engaged position"

SUMMARY OF THE INVENTION

The following describe some examples of embodiments of the invention. Other embodiments are within the scope of the description, including embodiments in which only some of the features from one example are used.

Other embodiments are within the scope of the description, including examples in which some of the features are selected from two or more examples.

Example 1. A wearable motion monitoring device comprising:

a housing sized and shaped to be positioned between a body region of a subject and a garment worn by the patient;

a marker comprised in said housing, said marker comprising at least one light emitter, wherein said light emitter is positioned to emit light from an upper surface of said marker, such that said at least one light emitter is indicative of displacements of said body region;

at least one garment holder incorporated in said housing, said holder serves as an anchoring point between said marker and said garment, said garment overlies said marker when anchored by said at least one garment holder.

Example 2. A wearable device according to example 1, wherein said housing comprises at least two garment holders, said holders are positioned at the periphery of said marker, at opposite sides of the periphery, such that a portion of said garment held by said at least two holders can be stretched between the two holders.

Example 3. A wearable device according to example 2, wherein said holders are arranged in a general shape of a polygon perimeter, such that said garment is stretched over the area of the polygon.

Example 4. A wearable device according to example 3, wherein said marker is positioned under the polygon so as to underlie a stretch portion of said garment.

Example 5. A wearable device according to example 3 or example 4, comprising a raised section of said marker, raised above said garment holders, so that said garment is stretched over said raised area when held by said holders.

Example 6. A wearable device according to any one of the previous examples, wherein each of said at least one said garment holder is attached to said garment from only one side of the garment.

Example 7. A wearable device according to any one of the previous examples, wherein at least one of said garment holders is attached to said garment from two opposite sides.

Example 8. A wearable device according to any one of the previous examples, wherein said marker has an upper surface facing said garment and a lower surface facing the body of said subject, the distance between said surfaces is less than 20 mm so that said marker is thin enough for said marker to be positioned between the body of the subject and the garment worn by said subject.

Example 9. A wearable device according to example 8, wherein said marker comprises at least two light emitters positioned to emit light from said upper surface of said marker, the distance between said at least two light emitters is between 5 mm and 30 mm.

Example 10. A wearable device according to any one of the previous examples, wherein said garment holder comprises a recess, said recess has an internal perimeter which is larger than an average finger-tip of an adult, said garment is pushed into said recess.

Example 11. A wearable device according to example 10, wherein said recess comprises at least one pawl, said pawl maintains a kink-resistance while bending.

Example 12. A wearable device according to any one of the previous examples, wherein said garment holder comprises an upper adhesive layer by which said holder attaches said garment, said adhesive suitable for removal without damaging said garment.

Example 13. A wearable device according to any one of the previous examples, wherein said garment holder comprises a separate frame which mounts on said marker, capturing said garment there between.

Example 14. A wearable device according to any one of the previous examples, wherein said housing comprises a lower adhesive layer by which said housing attaches to said body region.

Example 15. A wearable device according to any one of the previous examples, wherein said marker comprising:
control circuitry, electrically connected to said at least one light emitter;
communication circuitry, electrically connected to said control circuitry, wherein said communication circuitry receives and/or transmits wireless signals from and/or to at least one external device;
readable and/or writable memory circuitry electrically connected to said control circuitry,
wherein said memory stores one or more of indications of said control circuitry and/or at least one algorithm and/or sensed data.

Example 16. A wearable device according to example 15 wherein said at least one external device is also operable to output an alert when breathing problems are detected and/or when device malfunctioning is detected.

Example 17. A wearable device according to any one of the previous examples, wherein said marker comprises one or more motion sensor and/or inertial sensor.

Example 18. A wearable device according to any one of the previous examples, wherein said marker comprises one or more of magnetic sensors.

Example 19. A system comprising:
the marker of any of claims 1-18;
an imager;
a processor which receives from said imager one or more images of said marker and generates one or more signals indicating motion of said body.

Example 20. A wearable motion monitoring kit for stabilizing a motion marker, comprising:
a supporter, sized and shaped to be positioned between a thoracic body region of a subject and a marker housing;
said supporter has a surface texture and/or material which resists slipping relative to said body region;
a housing sized and shaped to be positioned between said supporter and a garment worn by said subject, said housing having a bottom surface suitable for not slipping relative to said supporter or said housing integrated into said supporter;
a movement marker including one or both of a sensor responsive to motion of said body and a light source which moves with said housing;
wherein said supporter transmits movements of said body region to said marker.

Example 21. A wearable motion monitoring kit according to example 20, wherein said supporter is adjustable in at least two dimensions to conform to a dimension said body region.

Example 22. A wearable motion monitoring kit according to any one of examples 20 to 21, wherein said supporter has an internal compartment defined by an external wall.

Example 23. A wearable motion monitoring kit according to example 22, wherein said housing is integrated into said supporter.

Example 24. A wearable motion monitoring kit according to example 22 or example 23, wherein the supporter is adjustable to conform to a curvature of said body region.

Example 25. A wearable motion monitoring kit according to any one of examples 20 to 24, wherein said supporter is at least 20 mm in thickness and wherein said supporter is more pliable than said housing.

Example 26. A wearable motion monitoring kit according to any one of examples 20 to 25, wherein said supporter comprises at least one adhesive layer suitable for temporary attachment to one or both of said body said housing.

Example 27. A wearable motion monitoring kit according to any one of examples 20 to 26, wherein said housing comprising at least one garment holder, said holder serving as an anchoring point between said marker and said garment.

Example 28. A wearable motion monitoring kit according to any one of examples 20 and 27, wherein said maker comprises at least one light emitters positioned to emit light form an upper surface of said marker.

Example 29. A wearable motion monitoring kit according to any one of examples 20 to 28, wherein said supporter is inflatable.

Example 30. A wearable motion monitoring kit according to any one of examples 20 to 29, wherein said supporter is in the form of a deformable pillow.

Example 31. A wearable motion monitoring kit according to any one of examples 20 to 30, wherein said marker comprising:
control circuitry, electrically connected to said at least one light emitter;
communication circuitry, electrically connected to said control circuitry, wherein said communication circuitry receives and/or transmits wireless signals from and/or to at least one external device;
processing circuity suitable for one or both of processing locally acquired signals and signals received over said communication circuitry.

Example 32. A wearable motion monitoring kit according to any one of examples 20 to 31, wherein said sensor comprises one or more inertial sensors.

Example 33. A wearable motion monitoring kit according to any one of examples 20 to 32, wherein said sensor comprises one or more magnetic sensors.

Example 34. A system for magnetically monitoring a subject's body motions comprising:
a wearable motion marker, said wearable marker comprising:
a housing shaped and sized to be attached to or form part of a garment worn by a subject;

a movement marker including one or both of a sensor responsive to motion of said body and a light source which moves with said housing;

a battery and a control circuitry housed in said marker, said battery and said control circuitry are electrically connected to said movement marker, for operating said light source emitter and/or sensor;

a magnet configured to be mounted on a human body or furniture which supports said body; said magnet and said wearable marker are not rigidly attached;

wherein, said magnetometer can detect movements of said magnet and thereby be sensitive to movements of said body.

Example 35. A system according to example 34, wherein said magnet is configured to be attached to a body.

Example 36. A system according to example 34, wherein said magnet is configured to be attached to a wearable item.

Example 37. A system according to any one of examples 34 to 36, wherein said wearable motion marker is provided with an at least one adhesive layer and is configured to be positioned in a desired body region of said subject.

Example 38. A system according to any one of examples 34 to 37, wherein said wearable motion marker comprising at least one garment holder incorporated in said housing, said holder serves as an anchoring point between said marker and said garment.

Example 39. A system according to any one of examples 34 to 38, wherein said control circuitry receives signals from said magnetometer and transmits said signals by a communication circuitry which is electrically connected to said control circuitry to a computerized unit.

Example 40. A system according to example 39, wherein said computerized unit analyses said signal and transmits said analyzed data to a user displaying unit.

Example 41. A system according to any one of examples 34 to 40, wherein said marker includes a light emitter configured to emit light from an upper surface of said marker.

Example 42. A system according to example 41, wherein said system comprising an image sensor, said image sensor detects a position or change in position of said light emitter.

Example 43. A system according to example 42, comprising a computerized unit configured to analyze signals received from said communication circuitry and said image sensor, determine one or more breathing parameter and send an indication thereof to a user displaying unit.

Example 44. A method of tracking breathing, comprising:
providing a system including a magnetic field sensor unit and a magnet unit;
attaching one of said units to a part of the patient which moves with breathing and the other of said units to a part of the patient or a fixture adjacent the patient which moves differently or does not move with said breathing;
tracking movement caused by said breathing, by analyzing a change in magnetic field detected by said magnetic field sensor unit;
processing said tracked movement to generate an indication regarding said breathing.

Example 45. A method for ameliorating interference with light emitted from a wearable body motion device, said method comprising:
positioning a light emitting marker between a body region of a subject and a portion of a garment worn by said subject, such that said light is transmitted through said garment;
reducing one or more of optical masking, scattering and variability in scattering or masking of said light by stretching said portion of said garment over a light emitting part of said marker;
detecting said emitted light by a sensor; and
analyzing said detected light by a computerized unit to identify one or more motion-related parameters of said body.

Example 46. A method according to example 45, wherein said subject is a non-human animal.

Example 47. A method according to example 45 or example 46, wherein said positioning comprises:
mounting said marker on a wearable housing, said housing comprises at least two garment holders;
anchoring said wearable housing to said garment by attaching said garment to said holders.

Example 48. A method according to example 47, wherein said at least two garment holders comprises one or more of a holder which traps a fold of the garment, an adhesive which undamagingly attaches to said garment and a two part holder which sandwiches a layer of garment between said two parts thereof.

Example 49. A method according to any of examples 45-48, wherein said stretching comprises reducing folds and/or wrinkles of said garment between said holders by attaching a first edge of said garment portion to a first holder, pulling said garment towards a second holder and attaching a second edge of said garment portion to said second holder.

Example 50. A method according to any one of examples 45 to 49, wherein said detection of said emitted light comprises, tracking the location of said light emitter by an image sensor Example 51. A method according to any one of examples 45 to 50, wherein said analyzing comprises estimating a tidal volume of breathing.

Example 52. A wearable motion monitoring device comprising:
a housing sized and shaped to be positioned between a body region of a subject and a garment worn by the patient;
a marker comprised in said housing, said marker comprising one or both of (a) a motion or physiological sensor and (b) at least one light emitter, wherein said light emitter is positioned to emit light from an upper surface of said marker, such that
said at least one light emitter is indicative of displacements of said body region;
at least one garment holder incorporated in said housing, said holder serves as an anchoring point between said marker and said garment, said garment overlies said marker when anchored by said at least one garment holder.

Example 53. A device for measuring a physiological characteristic comprising:
an attachment subsystem
a sensor and
a communication subsystem.

Example 54. The system of example 53, further comprising a processor configured to compute at least one of a volume of a physiological parameter, an alarm condition and a relative physiological parameter.

Example 55. The system of example 53, wherein said attachment system includes at least one of a skin adhesive, a connector to a piece of clothing and a wearable element.

Example 56. The system of example 53, wherein said sensor includes at least one of an image sensor overlooking the subject, a magnetometer, an accelerometer, a gyroscope, or a pressure sensor.

Example 57. The system of example 53, wherein said communication subsystem includes a radio transmitter.

Example 58. A method of detecting a physiological motion comprising:
positioning a sensor; and
measuring a physiological parameter with the sensor.

Example 59. The method of example 58, further comprising:
estimating a volume of a physiological movement.

Example 60. The method of example 58, wherein said positioning includes attaching said sensor to a human body with at least one of a skin adhesive and a wearable element.

Example 61. The method of example 58, further comprising:
transmitting said parameter.

Example 62. The method of example 58, further comprising:
alerting a person of an abnormal condition.

Example 63. The method of any of the above examples further including developing a classification scheme.

Example 64. The method of example 63, further including measuring simulating breathing and using simulated breathing measurements for said developing.

Example 65. A device for measuring a physiological characteristic comprising:
an attachment subsystem;
a sensor; and
a communication subsystem.

Example 66. The system of example 65, further comprising a processor configured to compute at least one of a volume of a physiological parameter, an alarm condition and a relative physiological parameter.

Example 67. The system of example 65, wherein said attachment system includes at least one of a skin adhesive and a wearable element.

Example 68. The system of example 65, wherein said sensor includes at least one of an image sensor overlooking the subject, a magnetometer, an accelerometer, a gyroscope, or a pressure sensor.

Example 69. The system of example 65, wherein said communication subsystem includes a radio transmitter.

Example 70. A method of detecting a physiological motion comprising:
positioning a sensor; and
measuring a physiological parameter with the sensor.

Example 71. The method of example 70, further comprising:
estimating a volume of a physiological movement.

Example 72. The method of example 70, wherein said positioning includes attaching said sensor to a human body with at least one of a skin adhesive and a wearable element.

Example 73. The method of example 70, further comprising:
transmitting said parameter.

Example 74. The method of example 70, further comprising:
alerting a person of an abnormal condition.

In some embodiments, the present invention describes a monitoring apparatus, method, and systems. More particularly, the invention describes a wearable device for monitoring motion which is related to physiological characteristics; in particular, those related to vital signs and breathing parameters.

In some embodiments, the present invention describes a system for monitoring physiological signals using a variety of sensors.

In some embodiments, the invention describes system architectures. In some embodiments, the invention describes means of physically holding a marker in place relative to a body part in various settings.

In some embodiments, the invention describes a 3D reconstruction of location of the monitored body region, for example reconstruction on the thorax movements of a subject during breathing, which is based on detecting the location of a single light emitter.

In some embodiments, the invention describes calculating "Volume Ratios"; Sensors and signal analysis; Intuitive user interface; and Learning schemes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In some embodiments, selected tasks according to some embodiments of the invention could be implemented as a plurality of software instructions being executed without an operating system at all like on a microcontroller unit Embedded in the wearable device. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as monitoring, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are described herein, by way of example only, with reference to the accompanying drawings.

With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 shows a side cross section of a patch comprising a marker positioned at an intermediate section of a housing (e.g., a patch), according to some embodiments of the invention;

FIG. 2A shows an exemplary embodiment of a side cross section of a patch comprising a reusable marker positioned at an intermediate section of the patch, said marker is positioned between an exemplary two griping sections;

FIG. 2B shows an exemplary embodiment of a side cross section of a patch comprising a reusable marker positioned at an intermediate section of the patch, said marker is positioned under an exemplary fixation element;

FIG. 3 shows a block diagram of a device including a marker and an attachment, according to some embodiments of the invention;

FIG. 4 shows an exemplary embodiment of a patch, for example as shown in Fig.1;

FIG. 5 shows an exemplary embodiment of a disassembled patch comprising a marker, positioned between three exemplary gripping elements, a reusable base and a sticker, according to some embodiments of the invention;

FIG. 6 is a flow chart of a method of positioning a wearable device on a garment, in accordance with some embodiments of the invention;

Figure 7A:
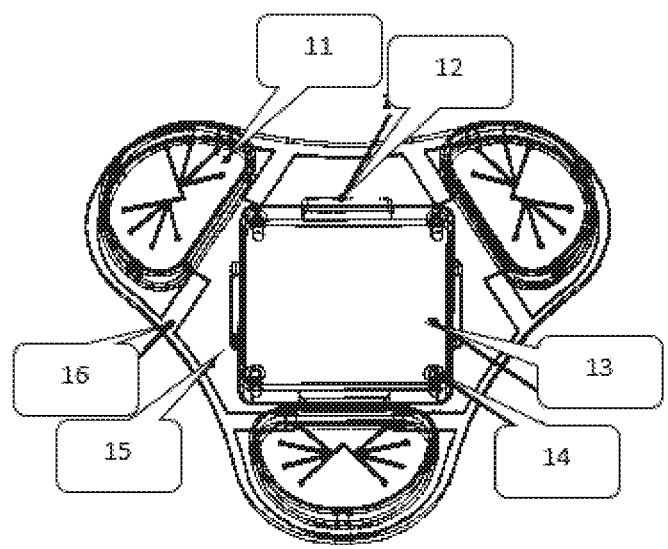
Figure 7B:
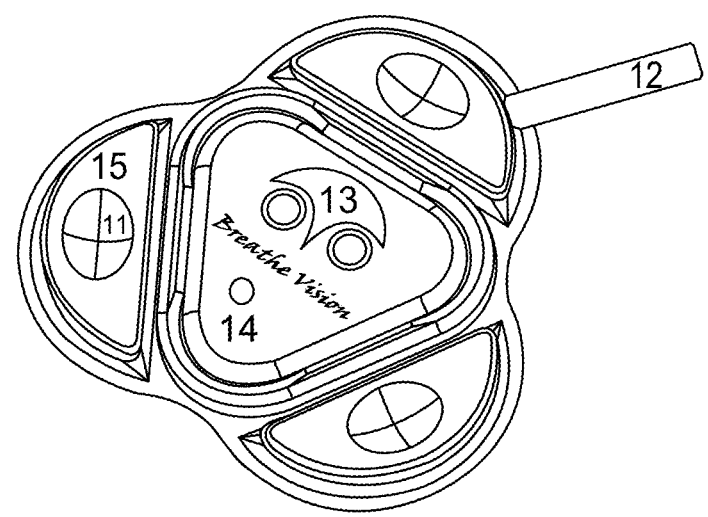
Figure 7C:
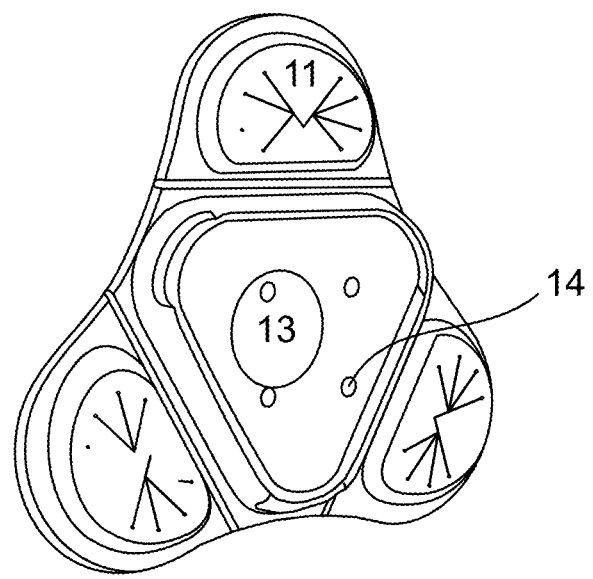
Figure 8B:
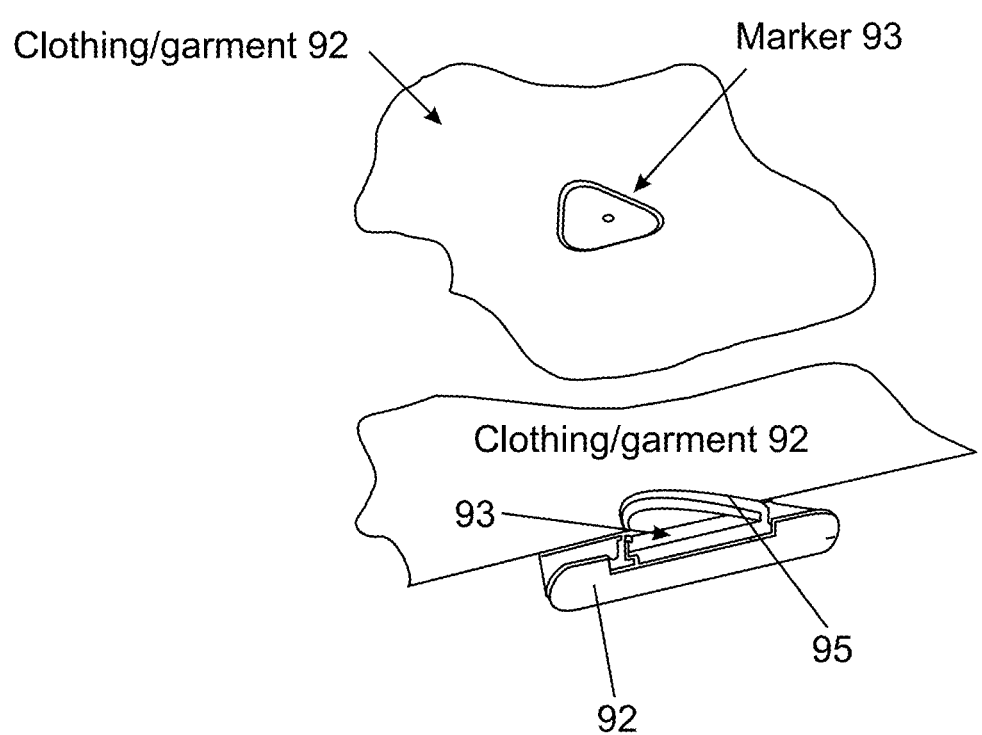
Figure 8C:
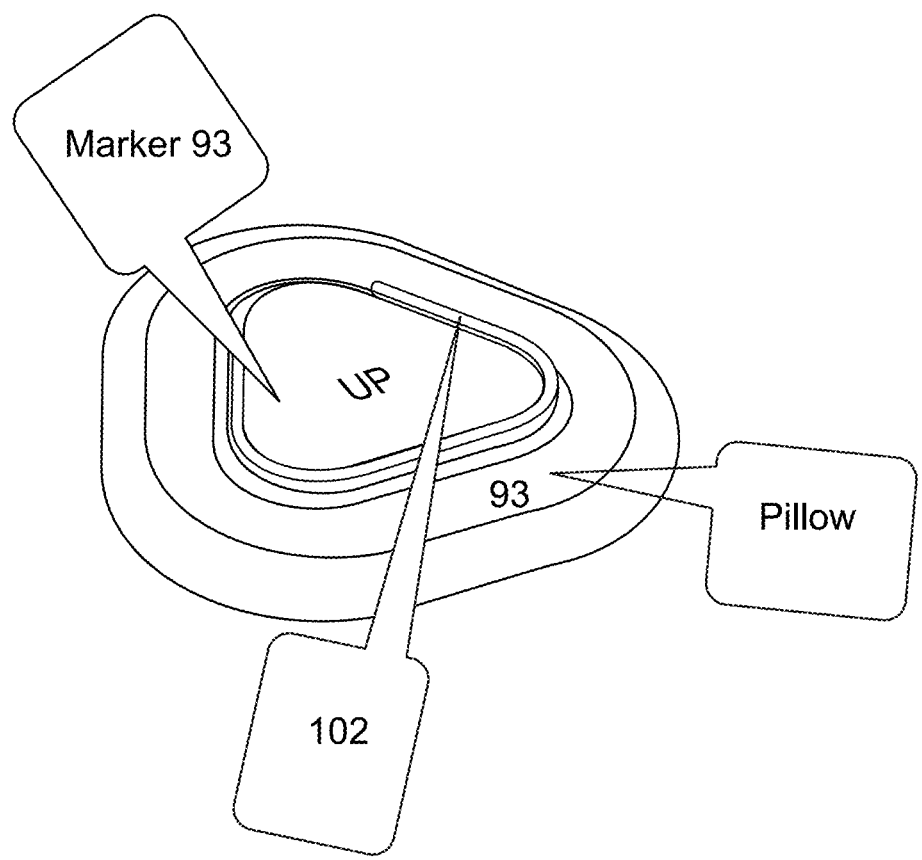
Figure 9A:
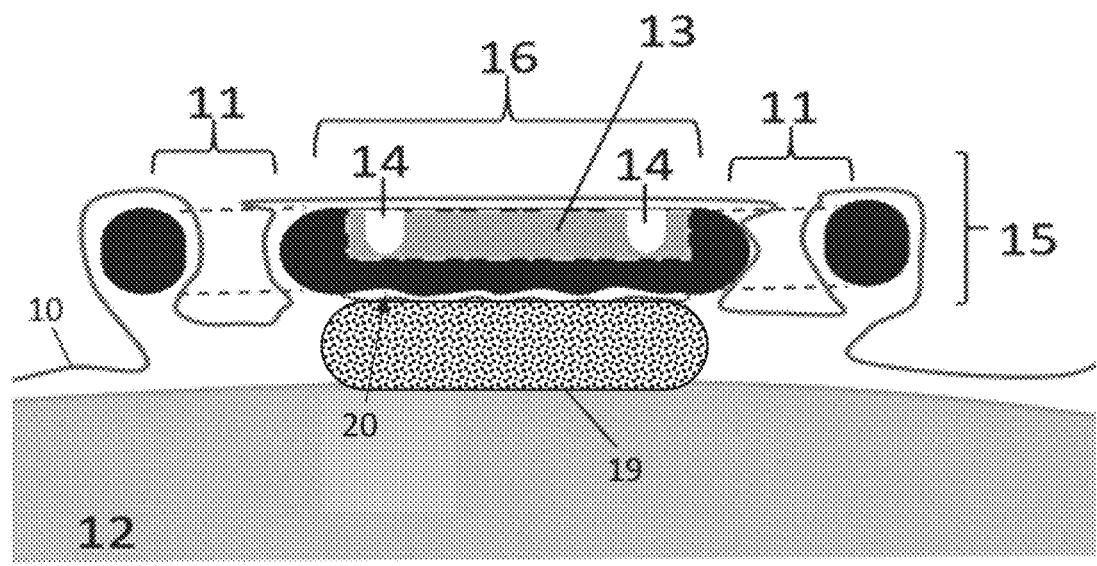
Figure 9B:
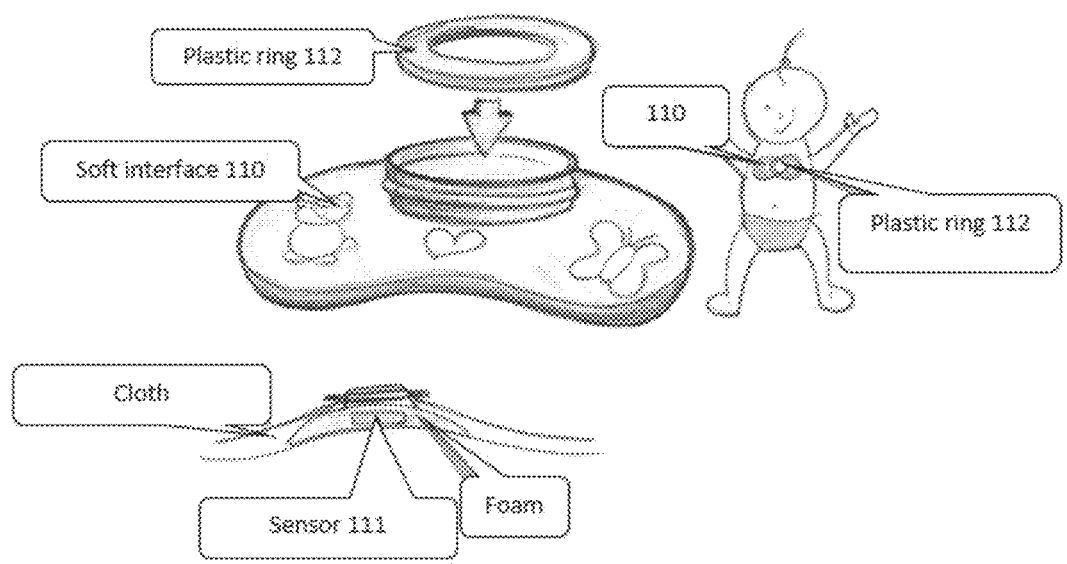
Figure 9C:
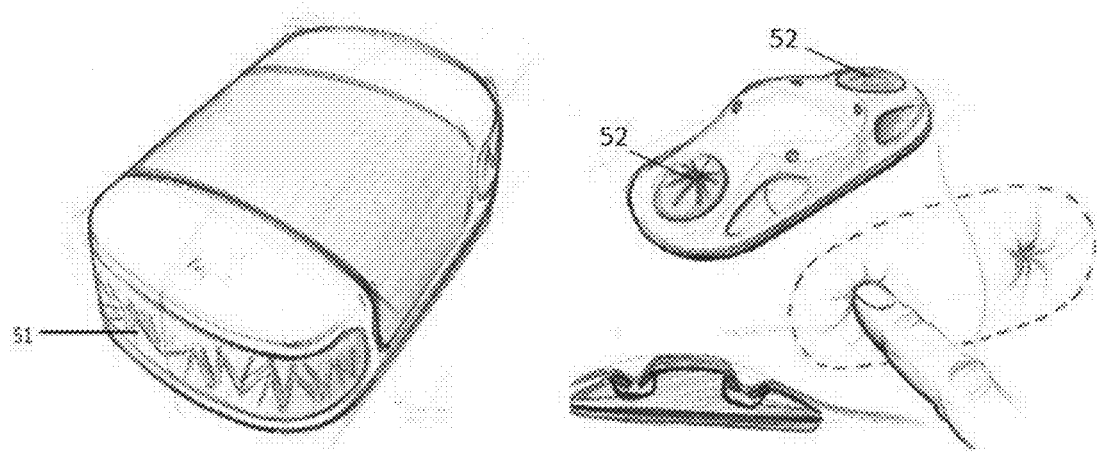
Figure 10A:
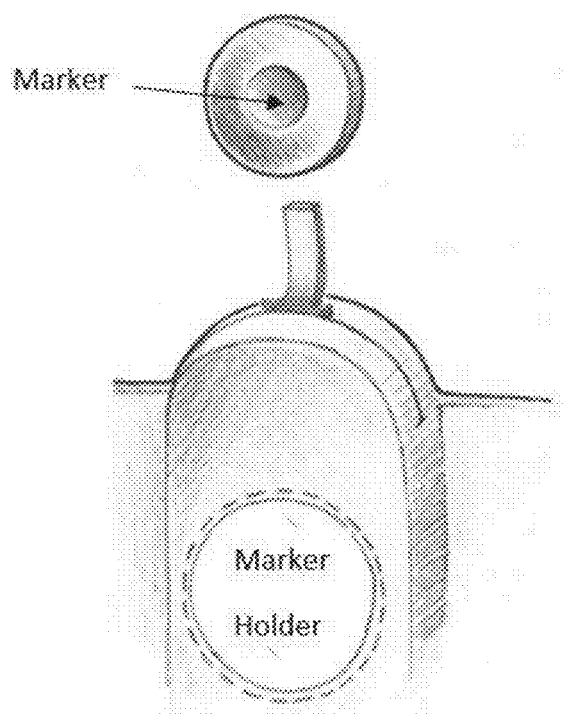
Figure 10B:
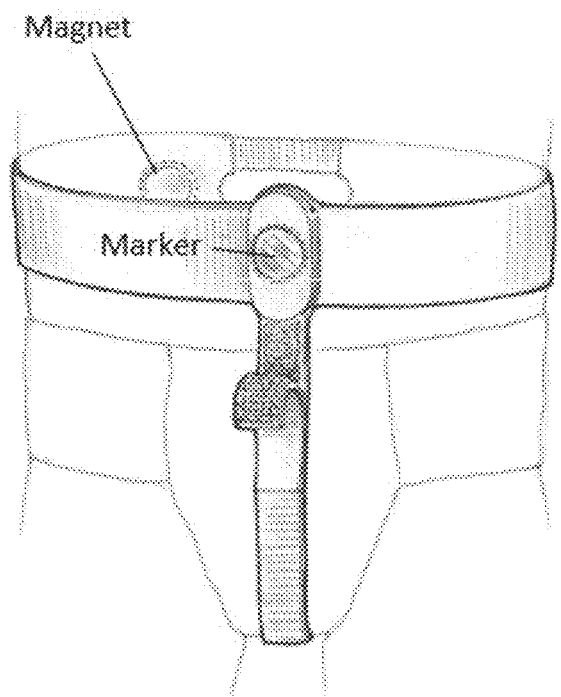
Figure 11A:
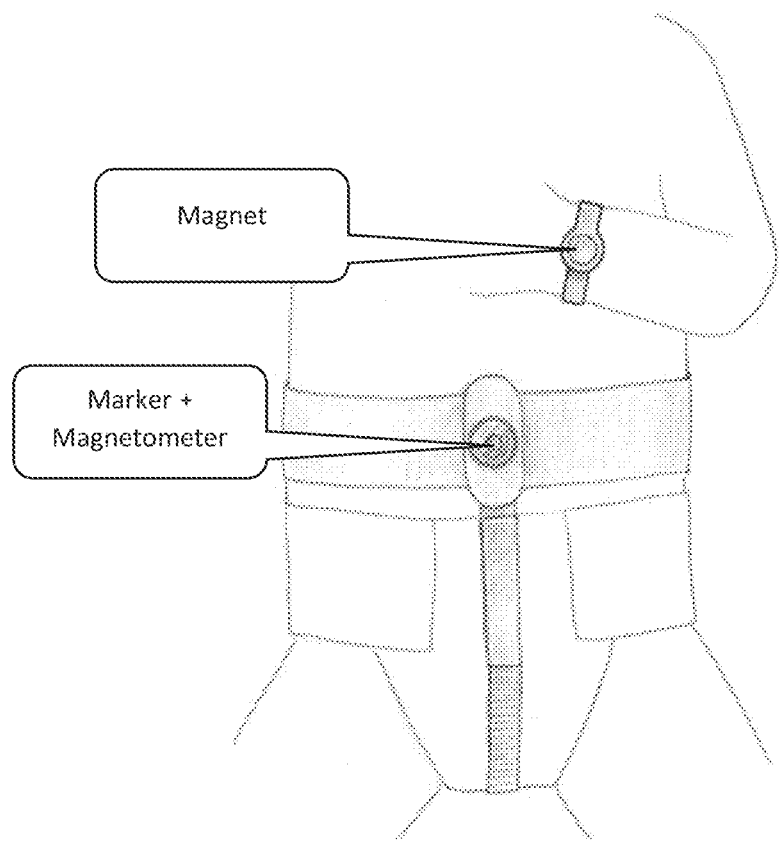
Figure 11B:
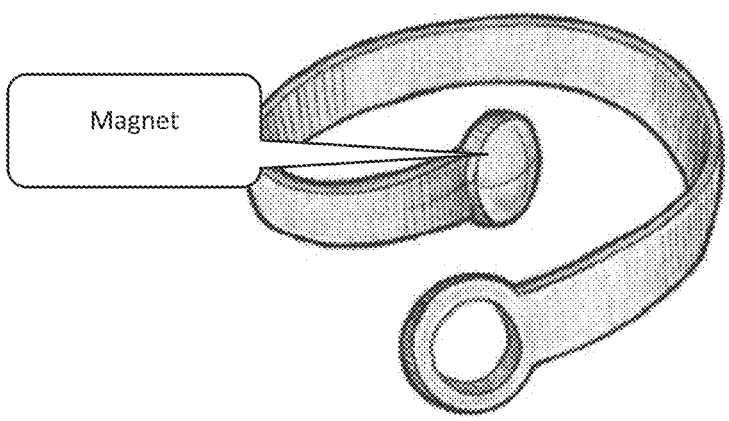
Figure 12:
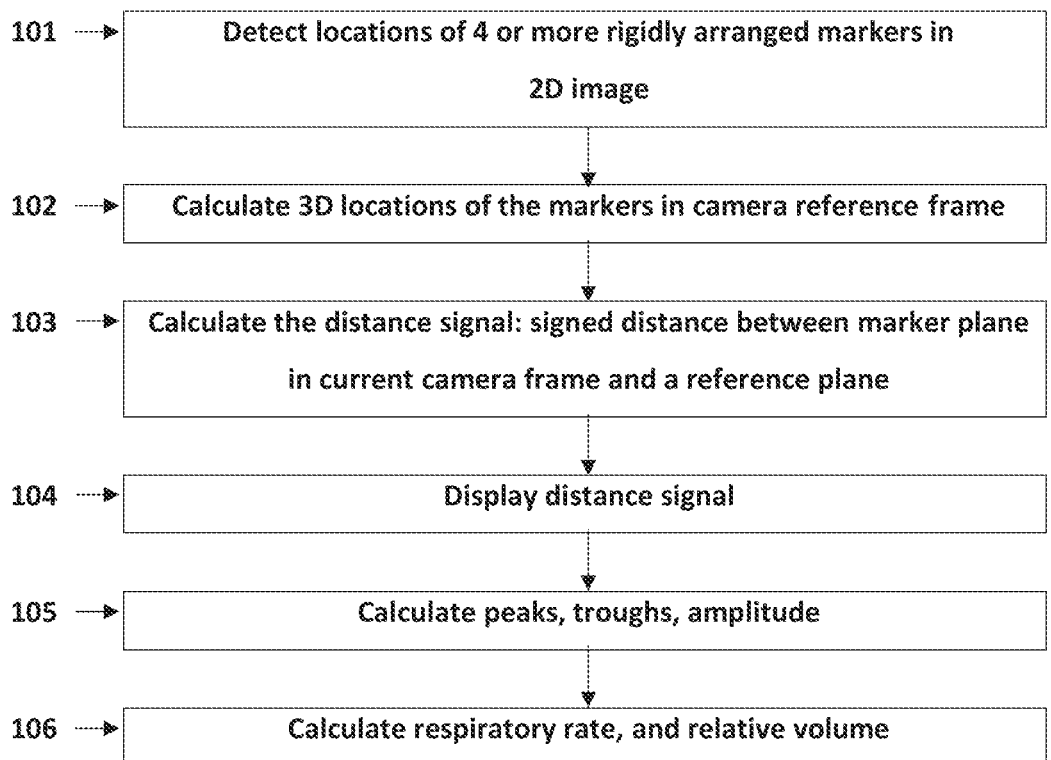
Figure 14A:
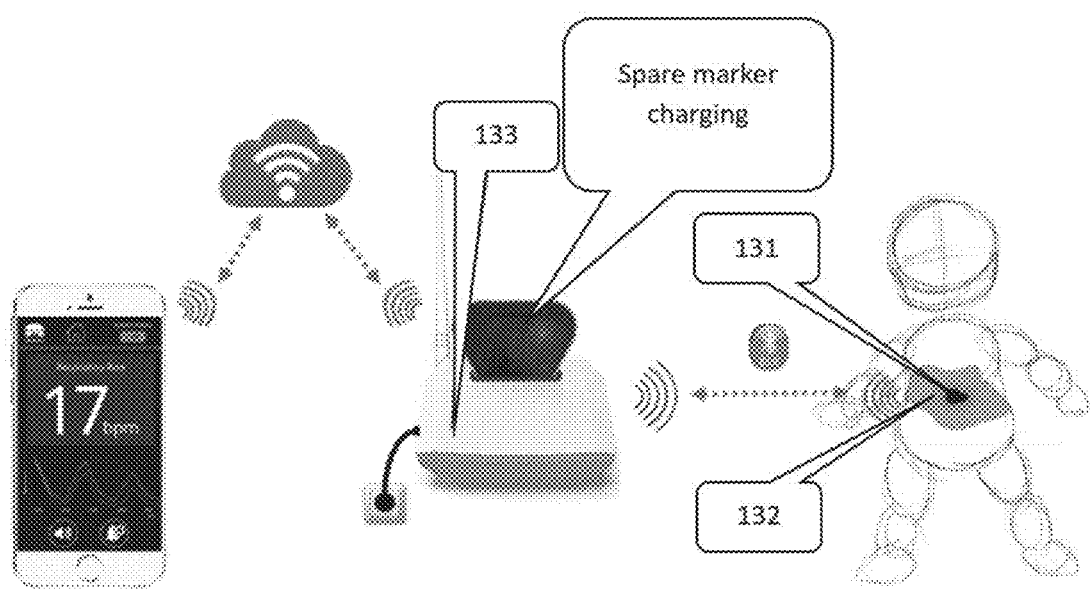
Figure 14B:
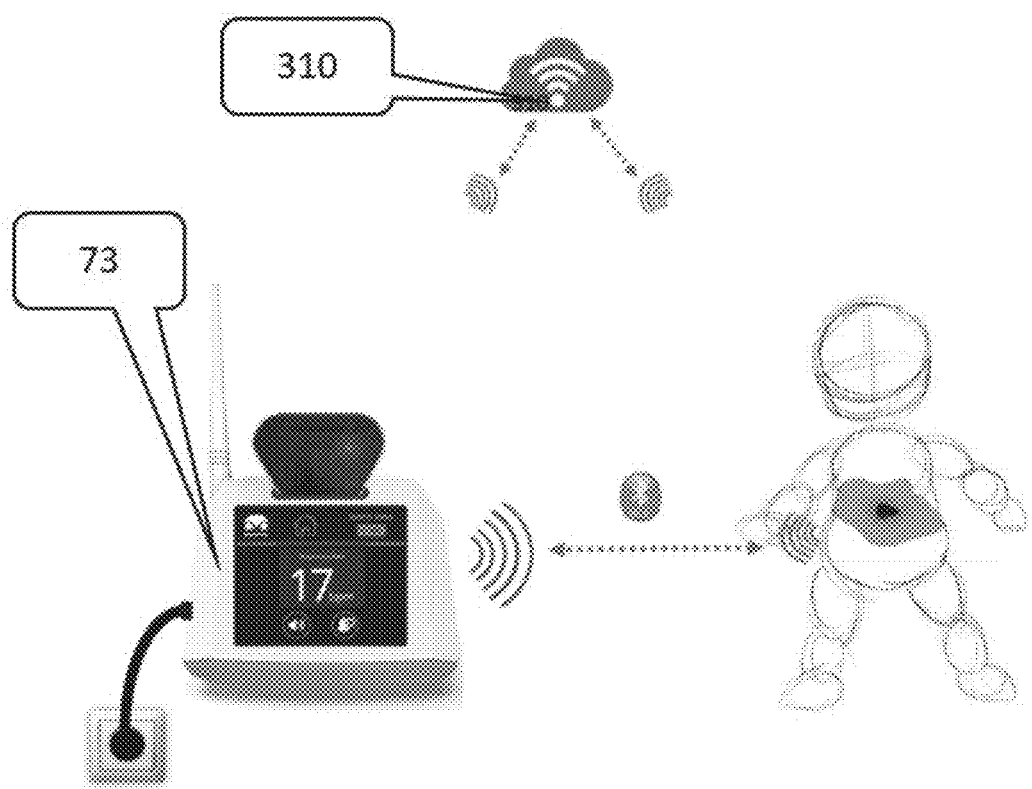
Figure 15A:
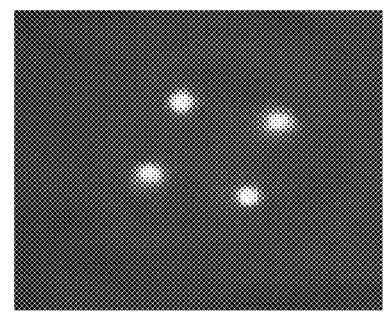
Figure 15B:
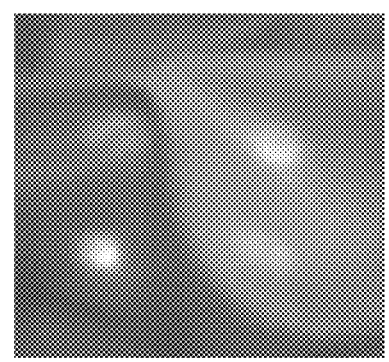
Figure 16:
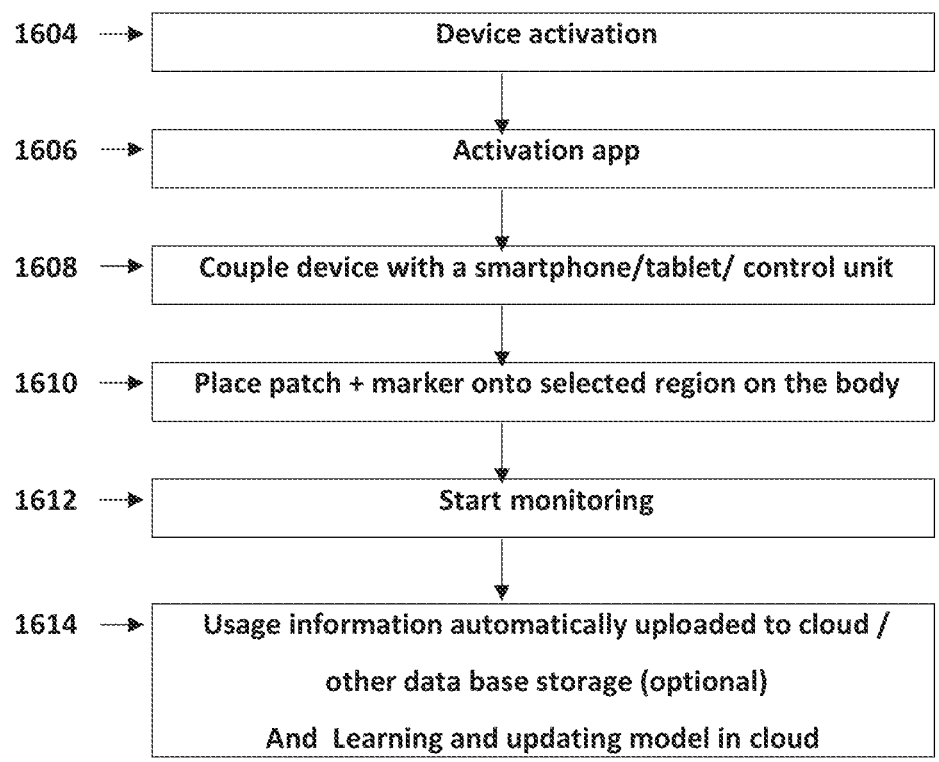
Figure 16B:
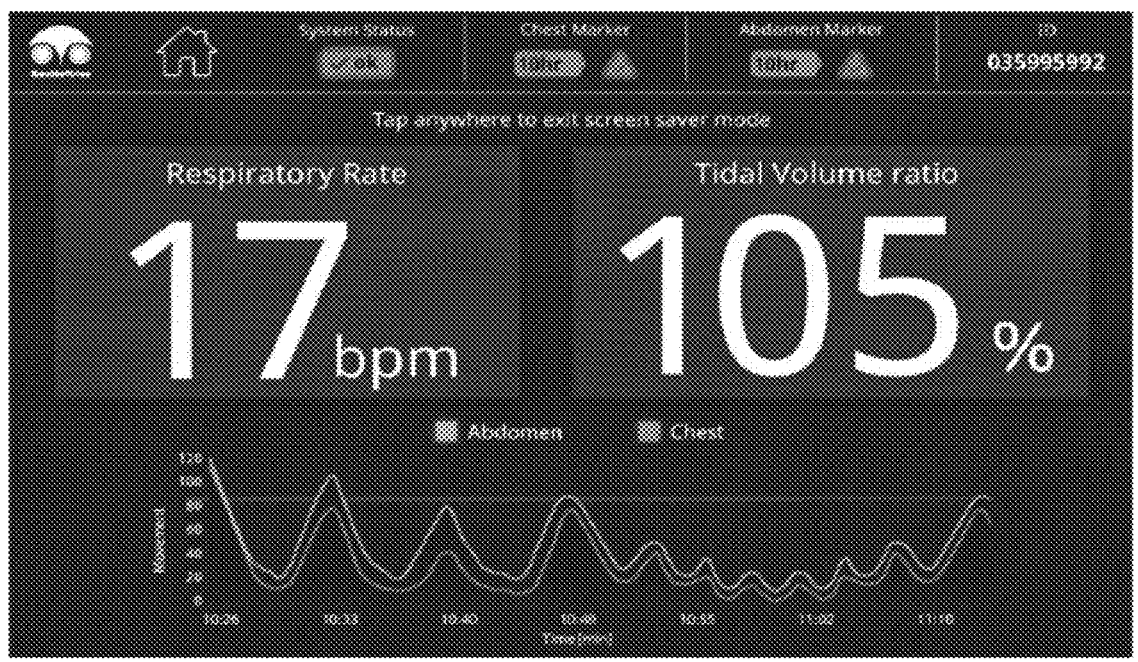
Figure 16C:
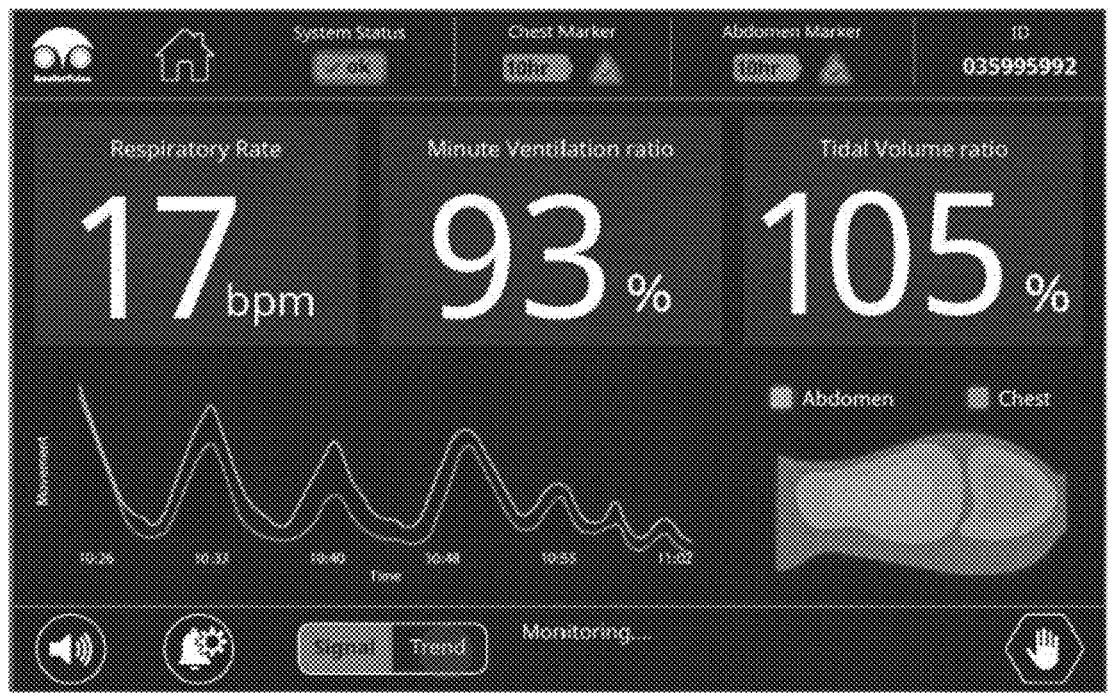
Figure 17:
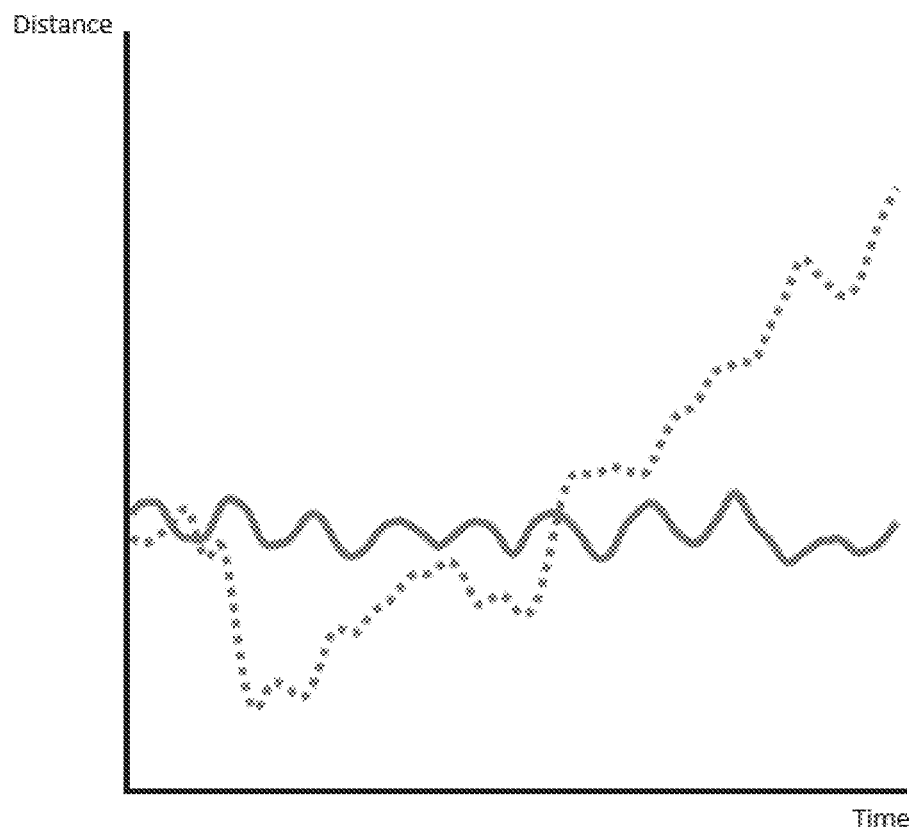
Figure 19C:
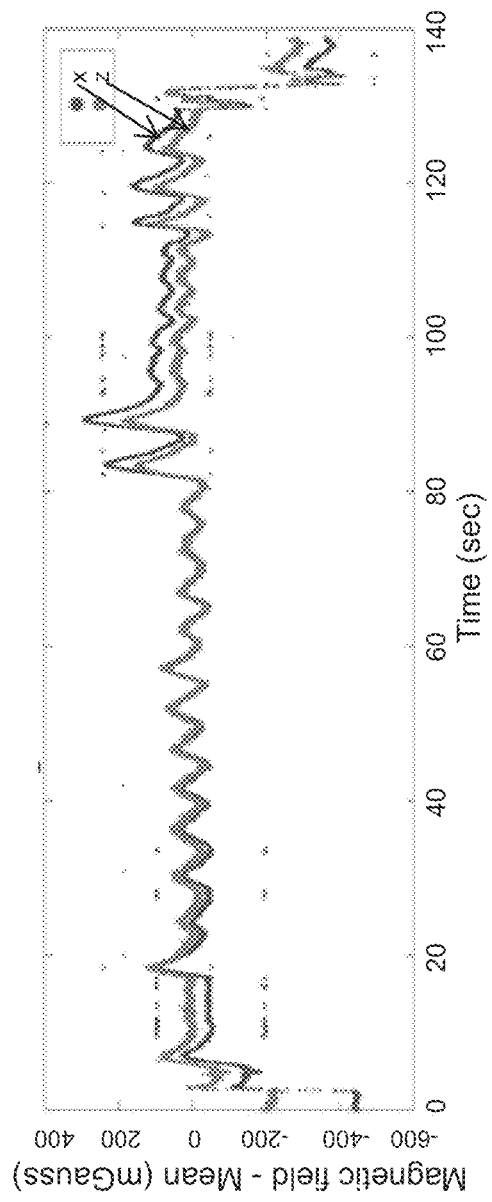

FIGS. 7A-B show an exemplary embodiment of a patch comprising a reusable marker positioned between three griping sections, according to one embodiment of the invention;

FIG. 7C shows an exemplary embodiment of a marker comprising a light emitter LED;

FIGS. 8A-C show an exemplary embodiment of a gripping element;

FIG. 9A shows a side cross section of a marker which is positioned on a supporter gripping said marker is positioned between an exemplary two gripping sections, according to some embodiments of the invention;

FIG. 9B shows an exemplary embodiment of a marker positioned between a garment and the body onto a supporter;

FIG. 9C shows exemplary embodiments of supporters;

FIGS. 10A-B show an exemplary embodiment of a marker positioned on a diaper and a magnetometer circuit positioned inside a marker holder connected to each other, according to some embodiments of the invention;

FIGS. 11A-B show an exemplary embodiment of a marker positioned on the stomach of a baby and a magnet positioned in a bracelet, in accordance with some embodiments of the invention;

FIG. 12 shows an exemplary flowchart of an analysis process of four markers, in accordance with some embodiments of the invention;

FIG. 13 shows an exemplary flowchart of an analysis process of at least one marker, in accordance with some embodiments of the invention;

FIG. 14A shows a schematic illustration of the device as part of a system, according to some embodiments of the invention;

FIG. 14B shows a schematic illustration of the device as part of a system, according to some embodiments of the invention;

FIG. 15A shows an exemplary embodiment of four light emitters positioned under an-unfolded (wrinkleless garment), in accordance with some embodiments of the invention;

FIG. 15B show an exemplary embodiment of four light emitters positioned under a wrinkled garment, in accordance with some embodiments of the invention;

FIG. 16A shows a flow chart of an exemplary activation method of the device by a user, in accordance with some embodiments of the invention;

FIGS. 16B-C show exemplary user interface displays, in accordance with some embodiments of the invention;

FIG. 17 shows an exemplary graph representing image processing results of a light emitter attached to the garment while being supported by a supporter, in accordance with some embodiments of the invention;

FIG. 18 shows a configuration of the magnet for movement sensing, in accordance with some embodiments of the invention;

FIG. 19A shows an IR sensor imaging breathing signals analysis, in accordance with some embodiments of the invention;

FIG. 19B shows a spirometer breathing signals analysis corresponding to that of FIG. 19A, representing the breathing volume of a patient, in accordance with some embodiments of the invention; and FIG. 19C shows a magnetometer breathing signals analysis corresponding to that of FIG. 19A, representing the breathing signal of a patient, in accordance with some embodiments of the invention;

DESCRIPTION OF SPECIFIC EMBODIMENTS OF THE INVENTION

The present invention, in some embodiments thereof, relates to monitoring apparatus, methods and systems. More particularly, some embodiments relate to a wearable device for monitoring motion which is related to physiological characteristics; in particular, those related to vital signs and breathing parameters.

Overview

An aspect of some embodiments of the invention relates to ameliorating the possible effects of physical interference with a light source used for monitoring body motions of a subject.

In some embodiments of the invention, the light source is located underneath a garment worn by a patient.

In some embodiments of the invention, physical interference is reduced in magnitude by manipulating said garment to prevent folds overlying said light source, for example by stretching the garment over said light source.

In some embodiments of the invention, variability in physical interference is reduced by stabilizing a portion of said garment overlying said light source, for example, by stretching the garment over said light source.

In some embodiments, light is emitted by the light source passes through the garment and received by a light detector. However, the light may be scattered and/or reflected and/or refracted while passing through said garment. In some embodiments, the scattering is modified by controlling the number and/or location of optical obstacles, such as garment folds, in the path taken by the emitted light.

In some embodiments, said number of optical obstacles is reduced by stretching the garment. For example, by anchoring the garment to at least two anchoring points. Optionally or alternatively, by first anchoring the garment to at least two anchoring points and after said garment is held by said two points, to a third anchoring point.

Optionally or alternatively, said garment may be positioned upon a flat surface, a convex surface or a frame.

In some embodiments, along with said positioning on said flat surface said garment is further anchored to anchoring points which are positioned at the periphery of said flat surface.

In some embodiments, said light source which is located underneath the garment is further attached to said garment by said anchoring points.

Optionally, said attachment is mechanical. For example, by a garment holder having a concave section into which the garment is pushed and held.

Optionally, said garment is held by two separated sections, positioned at opposite sides of the garment. For example, a lower section (e.g., a bulge) positioned underneath the garment and an upper section (e.g., a ring) which is mechanically coupled, for example by mechanical interference, with said lower section.

Optionally, said attachment is magnetic. For example, by a garment holder having two separated sections, positioned at opposite sides of the garment. For example, a first section comprising a metal positioned at one side of the garment and a second section comprising a magnet positioned at the other side of the garment.

Optionally or alternatively, said holder has an adhesive material which holds the garment while the garment is stretched in a desired manner onto the light source.

Stretching the garment allows forming a garment portion which has no wrinkles and/or folds and/or has wrinkles, folds and/or other unevenness which do not change to allow reducing the amount of obstacles and/or to prevent movements of the garment in relation to the light emitter. This may reduce degree and/or variability of scattering of the emitted light.

In some embodiments, the emitted light is detected by camera and/or by an image sensor and the location of the light emitter is reconstructed by a computerized algorithm.

In some embodiments, the manner by which a physical interference affects light detection (e.g., interferences by the garment and/or by other physical obstruction between sensor and light source) is analyzed by said computerized algorithm.

In some embodiments, said algorithm receives data which is acquired from said light source. In some embodiments, said data is compared to an external database and/or to a baseline.

In some embodiments, said reconstruction is based on analyzing the location of the light source by comparing the location of the detected light to a reference point.

Optionally or alternatively, said reconstruction is based on analyzing the location of the light source by comparing the location of the detected light with another light source having a known location.

In some embodiments, said reconstruction may be performed by analyzing the location of at least one light source.

Optionally or alternatively, said localization is performed by a continuous monitoring of the light source. Optionally or alternatively, said monitoring is performed at discrete time points.

An aspect of some embodiments of the invention relates to monitoring body motions of a subject by tracking signals received from at least one motion sensor and at least one light emitter.

In some embodiments, said motion sensor and said light emitter are positioned onto the body of a subject and move along with the movements of the body.

In some embodiments, the acquired data received from said sensors is analyzed by a computerized algorithm. Optionally, the analysis distinguishes breathing motions from non-breathing movements and/or is used to estimate tidal volume and/or other breathing parameters. In some embodiments, the analysis is based on data received from the light emitter. Optionally or alternatively, the analysis is based on data received from the motion sensor. Optionally or alternatively, the analysis is based both on data received both from the motion sensor and from the light emitter.

In some embodiments, said detected motions are movements of a subject's thorax. In some cases, such movements may be small and hard to detect and therefore each of said sensors may compensate the sensing limitations of the other.

In some embodiments, the subject pose is determined according to the light and/or motion sensors.

A potential advantage of acquiring signals from different types of sensors (e.g., light and motion) is the enhanced level of accuracy which is gained regarding of the subject's body motions.

For example an acquired IR signal which is represented by an image pixels, is detected by an image sensor. Said image sensor tracks the location of said light emitters.

As the thorax of a patient moves during breathing, so moves the location of the light emitter which is positioned onto the thorax of the patients.

Said movement of said light emitter is translated to motion movements and/or to tidal volume and/or breathing parameters which are presented to the user and/or to the caregiver in a displaying unit.

In some embodiments, the amplitude represents a distance between the location of the light emitter at the two point in the breathing cycle, for example between the beginning of inhale and the end of inhale.

Optionally or alternatively, a motion signal may be formed by detecting movements of a magnet positioned in a fixed location relativity to a magnetometer. As the subject breaths, the distance between the magnet and the magnetometer is modified. As such the magnetic altered field is detected by the magnetometer and a correlation between the IR signal and the magnetic signal is analyzed.

Optionally, the magnetic signal is used to calibrate the IR signal processing (e.g., to generate a translation table or function mapping movements or light positions to tidal volume).

Optionally or alternatively, a motion signal may be formed by detecting movements of a gyroscope and/or an accelerometer positioned for example inside said marker. As the subject moves (e.g., during breathing), movements of the body are detected by said motion sensor in all three axis (X, Y and Z). As such a correlation between the IR and/or magnetic signal and/or said sensors is analyzed.

Optionally, the IR sensor volume measurement is used to calibrate the gyroscope and/or an accelerometer signals (e.g., to generate a translation table or function mapping acceleration or angular rotation measurements to breath volumes).

In some embodiments of the invention, said marker may include a magnetometer and said body motions may be monitored by said magnetometer and without a light emitter.

Said marker may include a magnetic field sensor unit and a magnet unit. In some embodiments, said magnetic field sensor unit is attached to a part of the patient which moves with breathing and said magnet unit may be attached to other part of said patient.

In some embodiments, said magnet unit may be attached to a fixture adjacent the patient which moves differently or does not move with said breathing.

Optionally or alternatively, said magnet unit may be attached to the bed.

In some embodiments, tracking movement caused by said breathing may modify the magnetic field which is detected by said magnetic field sensor.

In some embodiments, said magnetic field sensor may produce signals which may be transmitted to a computerized unit for analyzing.

In some embodiments of the invention, said marker may include a magnetometer and said body motions may be monitored without a light emitter.

An aspect of some embodiments of the invention relates to stabilizing a marker attached to a garment worn by a patient, relative to a desired body location, using an intermediate supporter.

In some embodiments, said supporter stabilizes said marker on the desired body region and transmits movements of the body to the marker. Optionally, this allows the marker to be attached to a non-snug garment, and still reflect thorax movements due to breathing.

In some embodiments, said supporter can stabilizes a marker comprising for example a light emitter and/or a gyroscope and/or a magnetometer and/or an accelerometer.

In some embodiments, a continuous contact between the supporter and the body is preserved. In some embodiments, said continuous contact is also preserved between the marker and the supporter.

In some embodiments, said continuous contact between the supporter and the body is achieved by conforming the shape of the supporter to the curvature of the selected body region.

In some embodiments, said continuous contact between the supporter and the marker is achieved by adjusting the thickness of the supporter, said thickness is defined by the distance between the marker and the monitored body region.

A potential advantage of such conformity and/or adjustment is the enhanced stability of the supporter onto the selected body region which is gained, which further leads to enhanced stability of the marker while being positioned in respect to the desired body location.

In addition, stabilizing the marker to a desired location on the subject's body may allow a continuous monitoring of the body motions without damping of the signal, even in case when the subject poses changes. In such case, the marker will remain affixed to the monitored region and will continue to move according to the monitored body movements (e.g., the monitored breathing movements).

An aspect of some embodiments of the invention relates to supporting a marker at a spaced apart position from a body portion, for example, a thorax. In some embodiments of the invention, the marker is spaced apart by a soft supporter, for example, a supporter which can conform to the body and/or is deformable to do so. In some embodiments of the invention, the marker is attached to the supporter by friction using a housing, for example, the marker attached to a garment overlying the supporter, using a housing and, the housing being in a friction relationship with the supporter. Optionally or additionally, the housing is integrated into the supporter and forms a part of an upper side thereof.

In some embodiments of the invention, the marker is attached from an outside of the garment and snaps to geometrically interfere with a housing located on an inside of the garment.

In some embodiments of the invention, the supporter is a garment worn on the body, for example, a belt or a diaper.

In some embodiments of the invention, the marker includes a light source, movements of which can be detected using a spate optical sensor. Optionally or additionally, the marker includes other sensors, such as a movement sensor, a magnetometer and/or one or more physiological sensors such as an ECG or temperature sensor.

In some embodiments of the invention, the supporter is between 20 and 50 mm thick, while the marker and/or its housing are between 1 and 7 mm think. This may allow a marker to be coupled to the body without causing too much discomfort.

An aspect of some embodiments of the invention relates to stably and reversibly attaching a marker or other electronic circuitry to a garment. In some embodiments of the invention, the circuitry is attached to the garment using two or more spaced apart garment holder sections configured for reversibly attaching to a garment. In some embodiments of the invention, such attachment allows the garment to be stretched between the markers. Optionally or additionally, such attachment increases the degree to which movement of the circuitry correlates with movement of a body region under the garment, especially as relating to breathing motions or other motions of the thorax.

In some embodiments of the invention, the stretching and/or attachment at two spaced apart points (e.g., between 10 and 100 mm apart, for example, between 20 and 50 mm apart) provides a larger more rigid portion of the garment/ circuity combination, which moves as one. Optionally or additionally, the attachment at two spaced apart points increase a correlation between movement of the garment and movement of the circuitry.

In some embodiments of the invention, the garment holder comprises a frame which defines multiple spaced apart or a continuous attachment area between the garment and the circuitry.

An aspect of some embodiments of the invention relates to a body worn marker with circuitry which performs processing tasks for a system of separate components including the marker. It is noted that in parts of this specification the term "marker", especially when noted that a light source is optional, serves to also include an electronic circuitry unit.

In some embodiments of the invention, the system comprises an imager which images the marker and sends data to the marker. For example, the marker can receive position data or coordinates (e.g., of light sources of the marker) on an image and process such data to determine physiological movement parameters, such as breathing parameters, such as tidal volume. In another example, the marker receives physiological parameters and determines if to generate an alert. In another example, instructions to alert are sent form a system component to the marker, which displays (e.g., audio and/or visual) the alert. Optionally, the circuitry receives images, optionally compressed, from the imager and analyses them to detect the marker therein.

In another example, the system comprises a magnet, a magnetic sensor and one of the two is mechanically and/or electrically coupled to the circuitry. Optionally, the circuitry processes the change in magnetic field to determine a breathing parameter, for example, a tidal volume.

In some embodiments of the invention, data and/or commands are sent from one local component of the system, to another and then to a third or back to the first component (e.g., from marker, to imager to marker, or from imager to processing unit to marker.

An aspect of some embodiments of the invention relates to multi-point respiratory parameter determination, in which two markers are attached to a body or a garment and a single imager images both markers and determines a respiratory parameter, for example, a phase delay and/or other relative breathing parameter, from the difference in movement of the two markers, for example, a time delay between movement thereof. This method may also be applied if one or both of the markers detect movement using a movement sensor, such as an inertial senor such as a gyroscope or accelerometer, or using a two part sensor such as a magnet with a magnetic field sensor. Such movement detection may be instead of or in addition to light based detection of marker movement. In some embodiments of the invention, a single circuitry with a magnet or a magnetic sensor attached detects movement relative to two other components, each being a senor or a magnet (complementing the circuitry). Such double movement detection maybe used to extract one or more respiratory parameters.

It is noted that a particular advantage of some embodiments of the invention, in this aspect and others, is avoiding small system components and/or flexible system components which may be damaged (e.g., by having tension or shear or twisting applied thereto) and/or damage a patient (e.g., by swallowing or constraining flow in a body lumen surrounded thereby).

In some embodiments of the invention, a wearable marker system which is applicable to various settings and applications is described.

For example, for monitoring subjects who are undergoing sedative or pain killing treatment that can depress respiration.

In another example said system relates to monitoring deterioration in the chronically ill patients and/or to monitoring infants to protect against Sudden infant death syndrome (SIDS).

In some embodiments, the system serves as a diagnostic tool for sleep testing such as in cases of obstructive sleep apnea.

In such cases, the system can be used to track other movements in addition to respiratory movements, e.g., leg movements and eye movements, as well as for quantifying awakenings and sedation level. These can be important for sleep staging analysis.

Movements of body parts can provide much information on physiological characteristics such as sleep, breathing, tremors and more.

In some embodiments of the invention, a system which monitors the breathing of a subject using markers attached to the thorax of a patient is described.

In some embodiments, monitoring of movements of the chest is performed by using for example both optical and motion sensors, for example, inertial sensors.

In some embodiments, said motion sensors may include a magnetometer and/or an accelerometer and/or a piezo sensor.

In some embodiments, the system may include a spirometer for calibration.

In some embodiments, for accurate measurements, a marker is placed on the thorax of a patient, said marker should closely follow the movement of the body.

In some embodiments, the marker is attached to the body using a housing (e.g., a patch) or by using an elastic belt over the clothing and/or using adhesive.

In the case that the marker is attached to the body using a patch, the light (e.g. at emitted wavelengths at a useful amplitude) which is emitted from the marker, should pass through the clothing.

However, even when said clothing is transparent to said light, clothing and covers can move and fold over, causing the emitted light signals to scatter and/or otherwise become obstructed, leading to a weak and deformed signal pattern on the image sensor.

The result may be noisy and lead to an inaccurate location measurements obtained from the image sensor.

In some embodiments, one way of overcoming the scattering problem is to adhere the cloth covers in close proximity to the light emitters in a way that prevents any formation of folds in the cloth.

In some embodiments, the outer side of the patch (the side which is not facing the skin) has garment attachments in its circumference. In some embodiments, said attachments connect to the clothing and keep the clothing in place and stretched over the marker and its light emitting elements.

In some embodiments, the amount of tension which is applied to the skin is limited even in case where the clothing is pulled with significant force, thus avoiding discomfort and pain allowing the clothing to detach at a lower force.

In some embodiments, the amount of pull force transferred to the body sticker due to the pulling of clothing is limited by the fact that the attachment of the clothing to the patch is non-rigid and it may be partially released, yet will not damage standard hospital gowns and covers (e.g., cotton or polyester knit cloth).

In some embodiments, the system may be applied for monitoring for example a baby's motions and to produce alerts, for example, when breathing abnormalities are detected. For example, a baby monitor will be configured to alert on episodes of no breathing immediately, for example within 15 seconds and/or between 15 seconds and 1 minute. In some embodiments the alert can be produced if there are many "no breathing" episodes, where each episode may last only for a few seconds.

For example, fast warning of suspected cessation of breathing may give time to caregivers to take necessary actions in a timely fashion. Alerts of "no breath" should be accurate, since false alarms are a nuisance for the caregivers.

In some embodiments, the need to avoid false alarms may be particularly important in a home environment where care givers are sleeping.

For example, a home edition of the device may include a higher level of false alert protection than a hospital version. Alternatively or additionally, a baby-monitor may keep track of breathing signals or parameters, trends and/or anomalous breathing patterns.

This data optionally may be reported to the user.

In some embodiments, some data may include short term changes that are made available to the caregiver with little latency for example within 10 minutes and/or between 10 minutes to an hour and/or between 1 to 6 hours and/or between 6 to 24 hours. Long term trends of breathing pattern change and/or deterioration may be monitored from the baby monitor, for example in order to assist in diagnosing the onset of disease.

Exemplary Embodiments

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
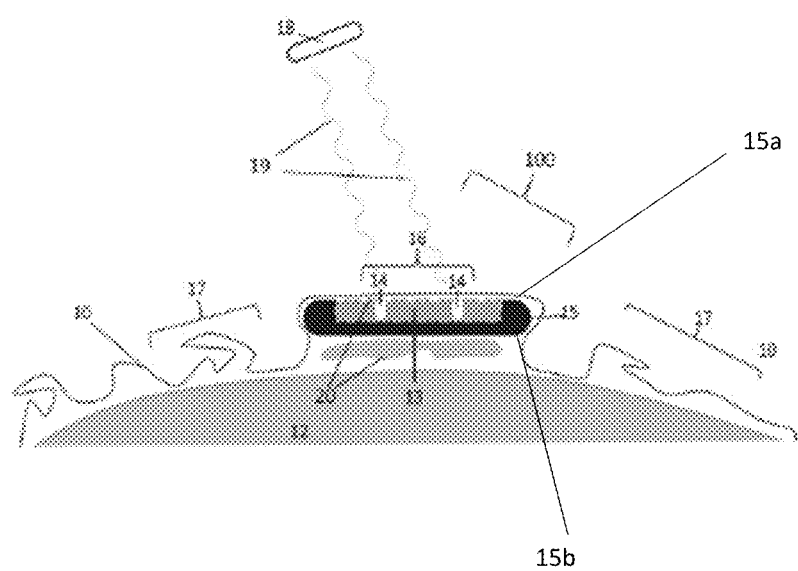

Referring now to FIG. 1, the figure illustrates a side cross section of a motion monitoring device 100 comprising an exemplary patch 15, and a reusable marker 13, which is held by said patch, in accordance with some embodiments of the invention. Said marker is optionally positioned at an intermediate section of said patch, such positioning may be, for example by integration or it may be separate connectable elements.

In some embodiments, said marker includes at least one light emitting element 14. Said emitted light may be an IR light emitter, said light is projected towards an image sensor, for example an image sensor 18.

In some embodiments, the patch is positioned under a garment 10 which covers a body 12 of a user. Said garment is positioned between the marker and the image sensor.

As garment 10 is positioned above patch 15, a portion of the garment is optionally stretched at an area 16 which is above the patch, where the marker is positioned. In some embodiments, said marker emits light towards said garment portion. This stretched and optionally un-wrinkled portion 16 reduces noise which arises from clothing and/or covers that moves and/or fold over, thereby possibly causing the emitted light signals 19 to scatter and/or become obstructed which may lead to a weak and/or deformed signal pattern which is detected on the image sensor 18.

Housing/Patch:

According to some embodiments, a patch 15 is positioned between a garment 10 and said selected body area 12.

In some embodiments, said patch align said marker in a stable position in respect to said garment.

In some embodiments, said marker 13 is further align by said patch in a desired orientation in relation to the image sensor 18.

According to some exemplary embodiments, device 100 comprises a thin housing (e.g., said patch) 15 having an upper face 15a and a lower face 15b. In some embodiments, the width, e.g., the distance between the upper face and the lower face, of the patch 15 is between 1 mm and 10 mm, for example between 3 mm and 8 mm, 4 mm and 7 mm, 5 mm and 8 mm, or any intermediate width.

A potential advantage of such a thin width is the enhanced comfort of positioning said device a body of a patient, which is gained by said thin width.

In some embodiments, device 100 and housing 15 are shaped and sized to allow a positioning entirely between the body of a patient 12 and a garment 10.

In some embodiments, the lower face of said housing (which facing the body), is shaped and sized to conform an anatomical curvature of the body, for example the curvature of the thorax. In some embodiments, said lower face has a flat face.

In some embodiments, housing 15 comprises an attachment element (for example element 11 at FIG. 2A) for attaching the upper face of housing 15 to a garment 10.

In some embodiments, garment 10 overlays said marker 13 and stretched onto patch 15 upper face.

Marker:

According to some exemplary embodiments, device 100 comprises a marker 13, positioned on and/or in said housing/patch 15.

In some embodiments, said marker 13 comprises at least one light emitting element, for example LED 14.

In some embodiments, said at least one LED is positioned on the upper face of the marker 13.

In some embodiments, more than one LED (e.g., 2, 3, 4 or more) is positioned on the upper face of the marker. In some embodiments, the LED's are positioned diagonally in respect to each other and/or in parallel in respect to each other.

In some embodiments, at least some of the LED's 14 emit Infrared light radiation.

A potential advantage of emitting infrared emitting is the enhanced permeability of such radiation through many types of garments.

In some embodiments, the LED's emit light which is detected by a detector, said infrared light radiation emitting distinguishes said light emitter from other light reflecting/emitting objects that reflect the visible light in the room (e.g., said upper flat face and/or the garment).

According to some exemplary embodiments, the LED's are positioned at a distance of at least 20 mm between each other, for example between 20 mm and 25, between 21 mm and 25, between 20 mm and 24, or any intermediate or larger distance.

In some embodiments, the attachment of patch 15 to a user body is performed by adhesive. For example, attachment patch 15 may comprise an adhesive layer (e.g., a hydrogel) positioned between the body and the patch 15. Optionally or alternatively, said layer is a sticker with glue. Optionally or alternatively, said sticker and/or adhesive layer is positioned at the lower side of patch 15 (e.g., element 20).

In some embodiments, said top surface of marker can (also) have adhesive on it.

Optionally or alternatively, an adhesive material is positioned at the interface between the patch 15 and the garment 10.

In some embodiments, said marker 13 may include at least one motion sensor. Said motion sensor may include a gyroscope, said gyroscope measure the orientation and angular velocity of the movements of a monitored body region in three axis, and/or an accelerometer said accelerometer measure the acceleration velocity of the movements of a monitored body region in three axis. In some embodiments, said marker 13 does not include a light emitting element. In some embodiments, said marker 13 includes a magnetometer, said magnetometer measures modifications in a magnetic field induced by a magnet which may be positioned in proximity with said magnetometer. In some embodiments, said marker 13 may include microphone and/or a speaker which may record breathing sounds. In some embodiments, said marker 13 may include pressure sensor, which may measure pressure induced by the movements of the selected body region.

Figure 2A:
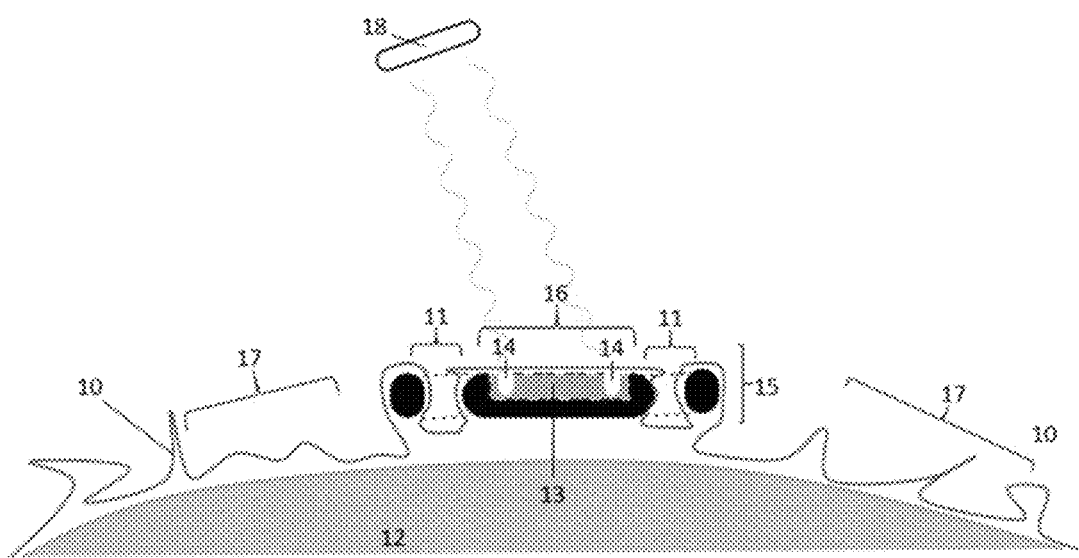

Referring now to FIG. 2A, the figure shows an exemplary embodiment of a side cross section of a patch comprising a reusable marker 13 positioned onto patch 15. In some embodiments, said marker is positioned between at least two attachments, for example attachments 11.

Garment Grippers:

In some embodiments, said patch comprises at least two attachments by which the patch 15 and the marker 13 are jointly anchored to a garment.

Said anchoring to the garment allows positioning said marker in a desired orientation in respect to an image sensor 18.

According to some exemplary embodiments, the attachments are positioned at a distance of at least 2 cm between each other, for example 7 cm between each other, 4 cm between each other 10 cm, or any intermediate or larger distance.

In some embodiments, said light emitters are positioned at an area between said attachments.

In some embodiments, each of the attachments comprises a recess to which the garment is pushed, for example the gripper described in U.S. Design Patent No. US D487,173 S.

In some embodiments, said recess is larger than an average fingertip of an adult, for example a recess is between 1.5 to 3 cm in diameter.

In some embodiments, such recess mechanically anchors the garment inside the recess. As such, a portion of the garment which is between the at least two attachments and above the marker is stretched.

In some embodiments, after a garment is pushed inside said recess, said garment is held inside said recess by at least one pawl. Optionally, said pawl is rigid. In some embodiments, said at least one pawl is connected to the inner perimeter of said recess.

Optionally or alternatively, said pawl bends when the garment is pushed into the recess.

Optionally, said pawl has a kink resistance. Said kink resistance is optionally sufficient to allow said pawl to recover its original shape (namely, an un-bended shape) when said garment is withdrawn from said recess.

In some embodiments, garment 10 serves as an anchoring point for the marker 13. In some embodiments, said anchoring allows reduction of bending and/or blurring and/or scattering of the light sources which may be caused by folds, wrinkles and/or other non-uniformities of the garment.

A potential advantage of positioning the light emitter under a stretched garment is the ability to more accurately reconstruct the light signal by the image detector 18.

A potential advantage of attaching the marker to the garment, arises from the ability to maintain said marker 13 in a known position, in respect to the image sensor 18.

Further, when held by the garment, and while being positioned on the body of a patient, the body movements of the patient can accurately be transferred to the marker. As the marker moves, so as the location of the emitted light which is further being detected by the image sensor 18.

Furthermore, aligning the movements with the movements of the marker may reduce the variability of the scattering of the emitted light and/or may enhance the accuracy of the body motion measurements.

Figure 2B:
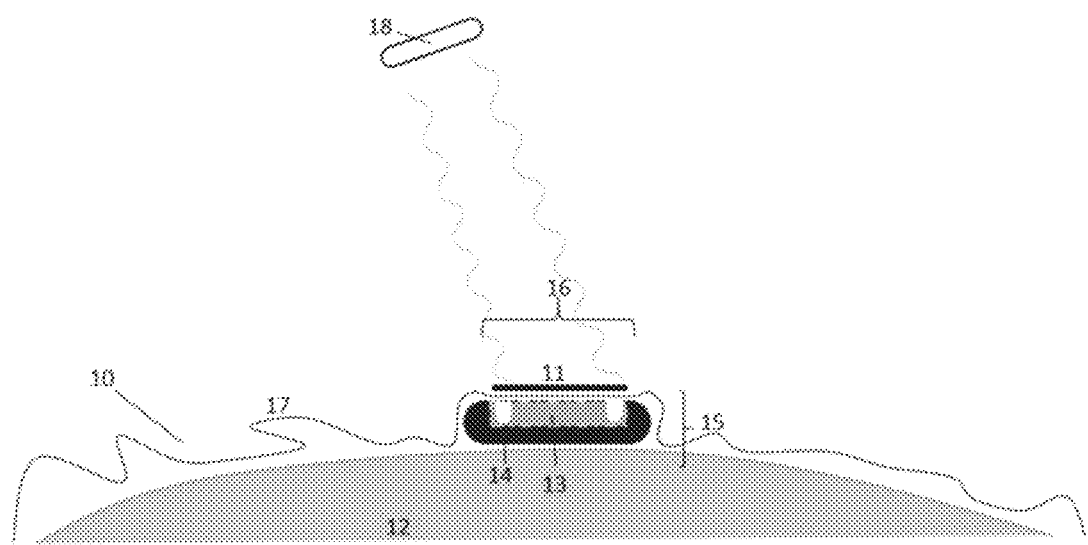

FIG. 2B shows an illustration of an exemplary attachment, by which patch 15 and marker 13 are anchored to the garment 10.

In some embodiments, patch 15 comprises a garment attachment which is divided to two parts.

For example to an upper part 11 which is positioned above the garment 11 and to a lower part which is positioned under the garment.

In some embodiments, said lower part is a portion of said marker 13.

Optionally or alternatively, said lower part is a portion of said patch 15.

In some embodiments, said upper part 11 may comprise a single piece. Optionally or alternatively, said upper part may be divided to more than one piece.

In some embodiments, said fixation element 11 is positioned on the garment 10, which is further held between said fixation element 11 and the upper flat face of said patch 15.

In some embodiments, said positioning of said fixation element 11 holds the garment 10 in a stretched manner onto the flat upper face of said marker 13, for example by friction and/or by being engages by matching protrusions and recesses on fixation element 11 and path 15.

In some embodiments, said fixation element 11 has a continuous annular shape.

Optionally or alternatively, said fixation element is shaped as a ring or a polygon, optionally with rounded corners.

In some embodiments, said fixation element 11 is a ring, positioned on top of the garment and locks the garment into the patch around the marker.

In some embodiments, the upper fixation element 11 has a recess which is defined by an external frame.

In some embodiments, the frame has a perimeter which is similar in its shape to the shape of the perimeter of the lower part (e.g., the marker upper surface).

In some embodiments, said perimeter of the frame may be slightly larger than the perimeter of the lower part (e.g., the perimeter of the upper face of said marker).

Optionally or alternatively, said perimeter of the frame may be slightly smaller than the perimeter of the lower part. As such, when the garment is placed over said lower part (e.g., above said marker), said upper frame may be pressed towards said lower part and to allow a mechanical grasp of the garment which positioned between the upper frame and the lower part.

In some embodiments, said frame by be elastic, as such, when pressed over said lower part and said garment, said frame may be enlarged and to grasp the garment which is located between the lower part and the frame firmly.

In some embodiments, said fixation element 11 and said lower part are mechanically coupled. Said mechanical coupling allows gripping a piece of garment.

In some embodiments, said external frame of said fixation element 11 is rigid.

Optionally or alternatively, said frame is elastic.

In some embodiments, said marker 13 is positioned under said garment 10 said garment overlays said marker. In some embodiments, said garment is stretched onto said marker and fixated firmly to the marker, while being stretched by said fixation element 11.

In some embodiments, said fixation is performed by gripping the garment from opposite sides by fixation element 11 from the one side and by the marker from the other side.

Figure 3:
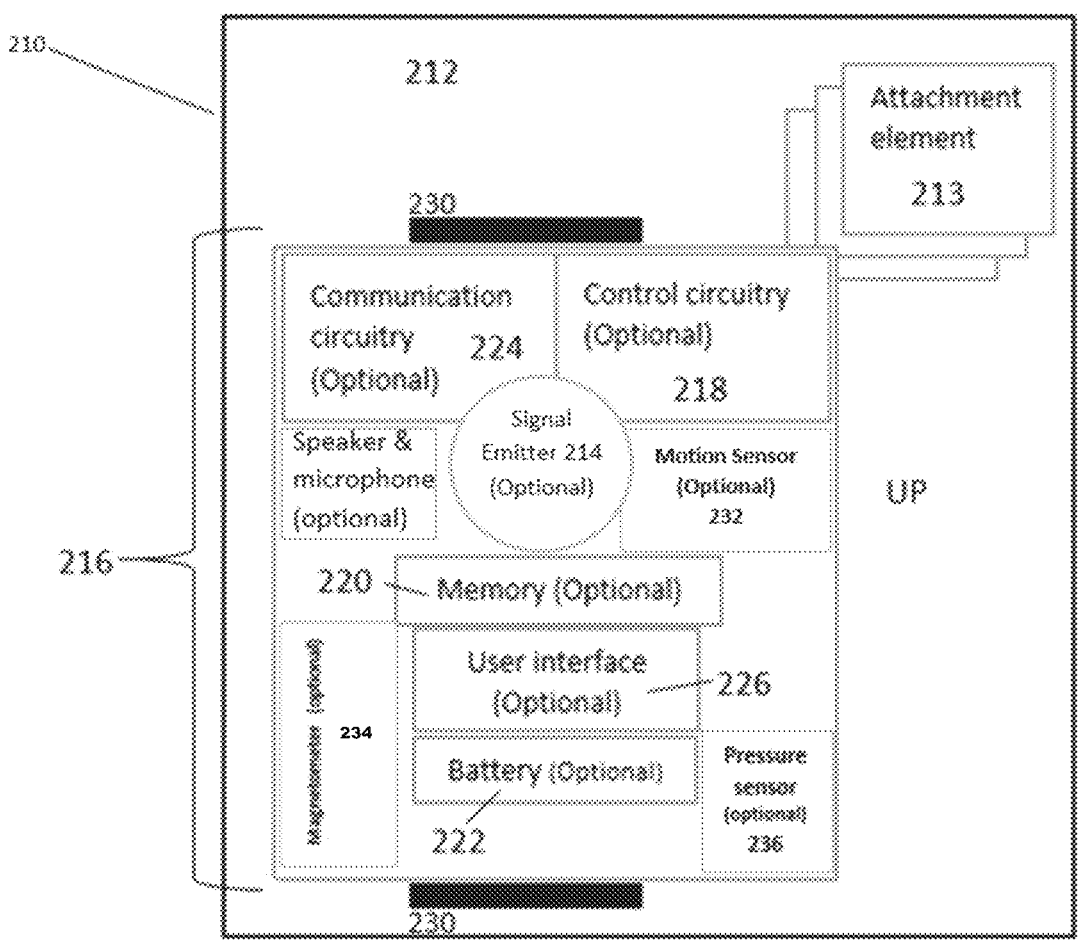

Referring now to FIG. 3. The figure shows a block diagram of a motion monitoring device 210 including a patch 212, a marker 216, and at least one attachment 213, according to some embodiments of the invention.

According to some embodiments, the device comprises a marker 216, mounted on a patch 212, said patch serves as a base for said marker 216.

According to some exemplary embodiments, a wearable monitoring device 210 comprises a thin patch 212 having an upper flat face, said upper face is facing a garment which overlies said patch (marked as UP) and a lower face which are facing the body of a subject.

In some embodiments, the marker 216 and the patch 212 are shaped and sized to be positioned between the body of the patient and a garment.

In some embodiments, the marker and/or its housing are between 1 and 7 mm think. In some embodiments, the marker has a planar flat shape. In some embodiments, said marker is a planar square. In some embodiments, the maximal length, which is defined by the distance between the edges of the marker of the marker is 10 cm.

In some embodiments, the patch 212 comprises an attachment element 213 for attachment via the upper flat face of the patch 212 to at least a portion of the garment.

Optionally an attachment element 213 is positioned on at least one location on the patch 212. In some embodiments, patch 212 comprises two or more attachments 213.

In some embodiments, said attachment element 213 stabilizes said marker in respect to a desired position in respect to the garment and/or in respect to a desired location of the user's body.

According to some exemplary embodiments, the wearable monitoring device 210 comprises at least one signal emitting element, for example LED 214.

In some embodiments, said LED 214 is positioned on the upper face of the marker 216.

Optionally, at least two LED's 214 are positioned on the upper face of marker 216.

In some embodiments, said signal emitting elements deliver the electric signal (e.g., IR signal) through a coupling layer. For example, such coupling layer may comprise a light pipe over the LEDs which can deliver the light to the surface of the garment. In some embodiments, said light tubed can deliver the light through the garment to the outer side of the garment.

In some embodiments, said coupling layer is positioned on top of the patch 212 and under the garment.

In some embodiments, the signal emitting elements 214 are positioned in a form of a polygon in relation to each other, for example in a form of a square and/or in a form of a rectangle. In some embodiments, the marker comprises 1, 2, 3, 4, 5, 6 LED's or any larger number of LED's.

In some embodiments, the device 210 comprise at least one sensing elements positioned at the upper and/or at the lower face of patch 212, for example a sensor to measure at least one physiological parameter of the body, for example heart rate and/or respiratory rate and/or tremor frequency and/or apnea events.

In some embodiments, the device 210 comprises at least one motion sensor, for example motion sensor 232. In some embodiments, said inertial sensor may include accelerometer and/or gyroscope by which the movement of the body is detected.

In some embodiments, the device 210 comprises at least one magnetic sensor. For example sensor 234. In some embodiments, said magnetic sensor may include magnetometer by which the movement of a magnet (e.g., attached to the body) is detected.

In some embodiments, said magnetometer may be positioned inside marker 216. In some embodiments, said magnetometer 234 may detect the presence of a magnetic field located in proximity to said magnetometer.

In some embodiments, such magnetic field may be originated by a magnet positioned either onto the body of a patient and/or near the patient.

In some embodiments, the magnetometer and the magnet are non-rigidly attached.

In some embodiments, as the detected region of the body moves, for example as the thorax moves during the breathing of a subject, the magnetometer moved accordingly and the distance between the magnet and the magnetometer alters, which can be detected by the magnetometer. In some embodiments, said magnetometer delivers a signal optionally to a communication circuitry 224 and/or to a control circuitry 218 for further processing. Optionally or alternatively, said communication circuitry 224 transmits a signal to an external device, for example to a computerized unit and/or to a mobile phone and/or to a cloud.

In some embodiments, said signals are transmitted to a displaying unit.

In some embodiments, the device 210 comprises at least one pressure sensor 236.

In some embodiments, a control circuitry, for example control circuitry 218 is electrically connected to said signal emitting elements 214.

In some embodiments, the control circuitry 218 controls the operation of signal emitting elements 214 according to at least one protocol stored in a memory 220, which is optionally a readable and writable memory.

In some embodiments, the control circuitry 218 controls the activation (e.g., turning ON and OFF) of an accelerometer and/or a magnetometer and/or gyroscope according to at least one protocol stored in a memory 220, which is optionally a readable and writable memory.

Optionally or alternatively, said control circuitry 218 receives signals from said accelerometer and/or a magnetometer and/or gyroscope which are detected by said motion sensors.

According to some exemplary embodiments, the monitoring device 210 comprises an interface 226, for example for receiving input from a user and/or for delivery of indications to the user.

In some embodiments, the interface comprises at least one light source, for example a display, for example, light emitting diode (LED) and/or at least one sound producing element.

In some embodiments, the interface 226 delivers indications which are related to the measured motion parameters (e.g., inertial parameters and/or magnetic field parameters and/or pressure parameters). In some embodiments, said indications are initiated by a pre-defined thresholds which are stored in said memory unit 220.

Alternatively or additionally, the interface 226 delivers indications (e.g., flashing or through sound) which are related to the operation status of the device 210, for example when the device is turned ON, and/or when the device delivers motion parameters, for example apnea and/or non-breathing/breathing motions and/or respiratory rate and/or when the device is in a non-monitoring mode.

In some embodiments, the interface 226 delivers alerts to a user, for example a 'low battery' alert and/or alerts related to device malfunctioning.

In some embodiments, the interface 226 delivers alerts to a user, for example breathing motion abnormalities.

According to some exemplary embodiments, the device 210 comprises a communication circuitry 224 which is electrically connected to the control circuitry 218 positioned inside the patch 212 and/or inside the marker 216.

In some embodiments, the communication circuitry 224 receives and/or transmits wireless signals, for example Bluetooth signals, Wi-Fi or any other wireless signals.

In some embodiments, the control circuitry comprises a receiver, for example for receiving the wireless signals from a remote device, for example from a wearable device (e.g., a bracelet) and/or from a mobile device.

Optionally, the receiver receives the wireless signals from a computer. In some embodiments, the communication circuitry 224 comprises a transmitter, for example for transmitting the wireless signals to a remote device, for example to a wearable device or to a mobile device. Optionally, the transmitter transmits the wireless signals to computer.

According to some exemplary embodiments, the device 210 comprises at least one battery, for example battery 222 which is positioned inside the patch 212. In some embodiments, said battery 222 is positioned inside the marker 216.

In some embodiments the battery 222 is a rechargeable battery, for example a lithium ion battery. In some embodiments, the battery 222 is remotely charged. Alternatively, the battery 222 is a non-rechargeable battery. Optionally, the battery is a thin battery, for example a coin or a disc shaped battery. In some embodiments, the battery 222 is a replaceable battery, for example a battery that can be replaced by the removal of a cover in the patch 212.

In some embodiments of the invention, signal emitter 214 transmit an Infra-red signal to an external detection unit, for example to an image sensor 18 (e.g., as shown at FIG. 1).

In some embodiments, more than one marker is incorporated onto a single patch. Optionally or alternatively, more than one marker is positioned on the body of a patient.

In some embodiments, markers may include a motion sensor, a processing unit, a wireless transmitter, and/or a rechargeable power source.

In some embodiments the system (which may include at least one marker and a sensing unit), includes a remote device which can communicate with said markers.

In some embodiments, said markers may also include a speaker and/or a magnetometer and/or led emitters.

In some embodiments, the holder/patch 212 is optionally soft and/or has a bracket for holding the marker, for example bracket 230.

In some embodiments, the holder/patch 212 and/or marker 216 are optionally washable in a washing machine, for example, being water insoluble and/or proof and/or resistant to effects of detergents.

In some embodiments, the marker communicates wirelessly to a base station 73 (shown for example in FIG. 14B) which is optionally located in the room and/or in another room (for example with the local caretaker).

The base station optionally includes a charger for recharging the marker.

For example, recharging may be performed when the marker is not in use. Recharging may be performed either wirelessly or through physical contact (e.g., marker including one or more electrode contacts on its surface).

In some embodiments, the base station is optionally connected to a network (for example the Internet) through a wired or wireless connection.

Alternatively or additionally, the base station may have a cellular connection capability.

Alerts and/or data from the sensors are optionally uploaded to a cloud (for example element 310 in FIG. 14A). For example, the data may be further analyzed and viewed by the caregiver remotely, for example on a remote mobile device.

In some embodiments, the base station 73 may also have a screen available for displaying the results.

Figure 4:
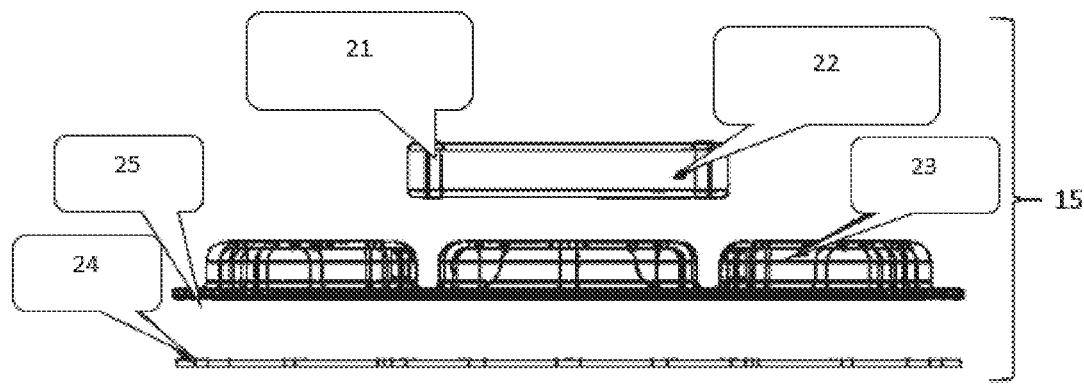

Referring now to FIG. 4. The figure shows an exemplary embodiment of a wearable monitoring device that includes a marker 22 and a patch 25.

The figure shows an exemplary cross-sectional view of the patch of FIG. 1.

The figure shows an illustration of an exemplary disassembled patch 15 comprising a marker 22, positioned between three exemplary gripping elements 23, according to some embodiments of the invention.

In some embodiments, marker 22 is a reusable marker. In some embodiments, the reusable marker 22 includes an infrared LED 21.

In some embodiments, the disposable patch 25 includes 3 attachments to clothing, one of which is attachment 23.

In some embodiments, a sticker 24 is adhered to the bottom of the disposable patch 25, said sticker is a removable sticker.

Stretching a garment over a marker:

In some embodiments, patch 15 is placed over a subject selected body area, with attachment 23 facing a garment worn by said subject.

In some embodiments, said patch is planar.

In some embodiments, said patch 15 comprises a marker holding section and at least two attachments. Optionally said patch 15 comprises three attachments, said attachments are positioned around said marker. Optionally said marker and attachments are positioned at the same plane. Optionally or alternatively, said marker protrudes above said attachments.

In some embodiments, said garment is attached to the said patch 25 and overlies marker 22 which is incorporated with said patch 15 at the middle of said patch 15.

In some embodiments, the garment is being anchored to a first attachment and pulled by the user towards a second attachment. Said pulling allows stretching of the garment over said marker and said planed patch.

After said first anchoring to a first attachment 23, the garment is anchored to a second attachment, and optionally to a third attachment.

Said pulling of said garment between the attachments and further anchoring the garment to the attachments, allows a fixated stretched garment positioned over the marker 22 and the light emitter 21 which is incorporated in said marker.

In some embodiments, said pulling the garment between said attachments allows fixation a fixed distance between the marker and the light emitters and the garment.

Figure 5:
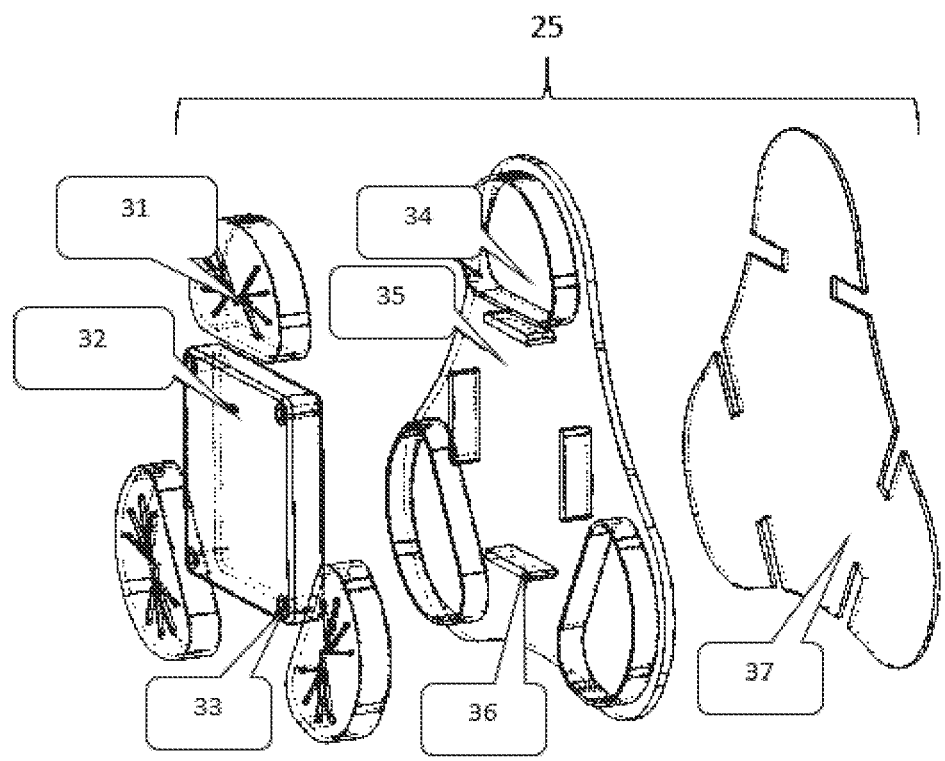

Referring now to FIG. 5. The figure shows an illustration of an exemplary disassembled patch 25 comprising a marker 32, positioned between three exemplary gripping elements 31, a reusable base 35, and a sticker 37, according to some embodiments of the invention.

In addition, patch 25 consists of disposable garment grippers 31 and a body sticker 37. In some embodiments, the reusable marker includes LED's 33 and holder 36 for marker 32.

In some embodiments, the clothing or covers are inserted into the patch 25 by pushing at least a portion of the clothing or covers with a finger into attachments 31.

Figure 6:
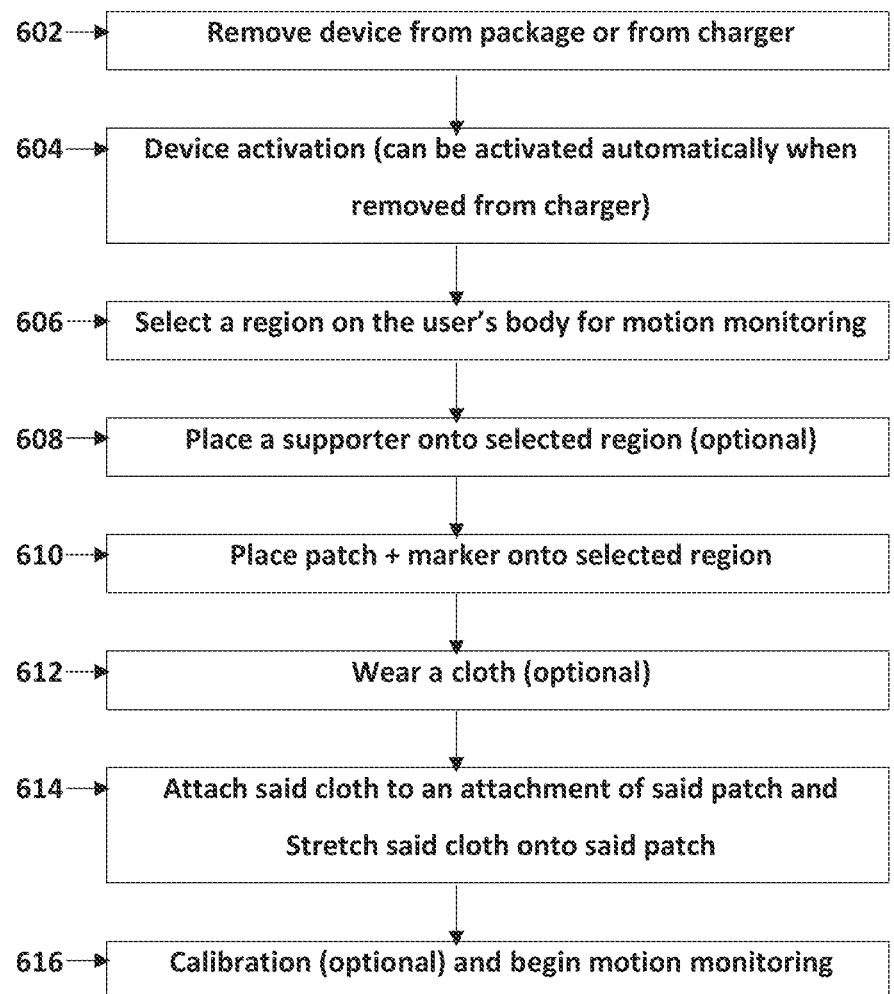

Referring now to FIG. 6, the figure is a flowchart of an exemplary process of positioning a motion monitoring device on the body of a patient. In some embodiments, said device is anchored to a desired orientation in respect to an image sensor by a garment.

According to some exemplary embodiments, the motion monitoring device along with the patch (e.g., a wearable patch) and marker are easily applied to the garment and should be easily activated, in order to reduce discomfort of a subject.

Easy activation and reduced discomfort may have a significant importance when applying said device for example to babies, which often tend to move.

Optionally or alternatively, said activation is performed wireless. For example from a mobile device and/or an external remote station.

At 602, an exemplary motion monitoring device is described. Said device is removed from a package. Optionally or alternatively, said device is disconnected from a charger.

Referring now to FIG. 7A.

The figure shows an exemplary embodiment of a motion monitoring device, comprising a marker 13. In some embodiments, said marker is positioned on a patch 15. In some embodiments, said patch 15 has at least one garment gripping element 11, by which a stable positioning of the marker is gained.

In some embodiments, said disposable patch 15 holds the marker 13 which includes light emitting elements. In some embodiments, said light emitting element is an infrared LED 14.

In some embodiments, the clothing or covers are inserted into the patch 15 by pushing at least a portion of the garment with a finger into attachments 11. In some embodiments, attachment 11 is an integral part of patch 15.

In some embodiments, protrusions of the patch, such as 12, are used to hold the markers in place, and possibly other elements needed such as a permanent magnet (further elaboration regarding said magnet is described herein below).

Optionally or alternatively, the patch 15 is adhered to the body using a two-sided sticker. For example sticker 16 is positioned on the surface of the patch at an opposite side in respect to the marker 13.

In some embodiments, said sticker 16 has a cover which is removed prior positioning of the patch onto a patient body. In some embodiments, said sticker has an adhesive at its surface by which a stable positioning of the patch and marker to the body is achieved.

A potential advantage of using a sticker is the enhanced stability of the marker to the body. In some embodiments, such stability may provide an enhanced accurate extrapolation of the measured physiological parameters of the patient.

In some embodiments, the device is a single-use device that is used, for example for several hours, and then it is discarded. Alternatively, the device is removed from the body of the patient and is stored in the package for further usage.

In some embodiments, the patch is disposable and the marker is reusable.

According to some exemplary embodiments, the device is activated at 604.

In some embodiments, the device is activated by pressing an activating button.

Optionally or alternatively, the device is activated automatically when removed from charger. Alternatively, the device is activated by removing a separating insulator between a battery and electrical conductors.

In some embodiments, the device is activated by inserting a battery into the device.

In some embodiments, the device is activated while removing the device from the package at 602. Optionally, the device delivers an indication by light and/or by sound when the device is activated.

According to some exemplary embodiments, an application program installed on a mobile device, for example a smartphone, a tablet and/or a smartwatch delivers an indication to a user to activate the device. In some embodiments, the mobile device delivers the indication based on an algorithm and/or tables stored in the memory of the mobile device.

Referring to FIG. 7C, the figure shows an exemplary embodiment of a motion monitoring device comprising a marker 13. In some embodiments, said marker 13 comprising a plurality of light emitter LEDs 14.

In some embodiments, activation of the device, may activate at least one LED among said light emitter LEDs.

According to some exemplary embodiments, the device is attached and/or placed on the user body at 606.

In some embodiments, said motion monitoring device is placed onto the chest area of the monitored patient. Optionally, the device is placed onto the back of the patient. In some embodiments of the invention, the placement location depends on the current or expected posture of the patient (e.g., sitting, lying on back, lying on stomach, lying on side).

In some embodiments of the invention, motions of the patient are monitored by analyzing movements of other parts of said patient body. For example, motions of the limbs and/or head of the patient.

In some embodiments, said motion monitoring device is placed onto a planar part of the body, for example, onto the thorax area.

In some embodiments, said device is positioned on a curved part of the body.

In some embodiments, the motion monitoring device is attached directly to the body of the patient, optionally said attachment is performed by adhesive materials. Optionally or alternatively, the device is placed on the body, and is kept is a stable position by attachment to a portion of the garment.

In some embodiments, the device is placed on the body when the patient is in supine position. Optionally or alternatively, said positioning is performed when the patient is sitting and/or when in a standing position.

At 608, according to some exemplary embodiments, the device is attached and/or placed on a supporter, said supporter is placed between the user body and the monitoring device.

Referring now to FIG. 9A, the figure shows a schematic representation of a side cross section view of a patch 15 comprising a reusable marker 13.

In some embodiments, said marker 13 is positioned at an intermediate section of the patch 15. In some embodiments, said marker is positioned on a supporter, for example a supporting pillow 19. In some embodiments, said pillow is positioned between the body 12 and the patch 15.

In some embodiments, said supporting pillow has an external wall and an inner compartment. In some embodiments, said inner wall and said inner compartment are made of the same material. Optionally or alternatively, said inner compartment and said external wall are made of a different materials. In some embodiments, said external wall is more rigid than said inner compartment.

Optionally or alternatively, said external wall is elastic. Optionally said external wall is made of silicon.

Optionally or alternatively, said pillow is filled with soft materials therein.

In some embodiments, said inner compartment comprises a foam, optionally a memory foam, optionally or alternatively, said inner comportment is filled with Silicone gel and/or foam and/or bubble foam.

Optionally or alternatively, said inner compartment includes an elastic pellets and/or a powder which allow modifying the shape of said pillow.

In some embodiments, said filling of said inner compartment, packed by said elastic external wall allows adjusting the shape of the pillow, by pressing the pillow to a desired shape.

In some embodiments, said supporting pillow has a lumen defined by said external wall.

In some embodiments, said marker 13 is positioned between an exemplary at least two garment griping sections/attachments, for example attachments 11.

In some embodiments, said exemplary supporting pillow 19 provides a stable positioning of the marker 13. Further, being placed onto the patient body, said pillow transmits breathing motions and/or other body motions to the attached marker. As the pillow moves, the marker moves respectively.

In some embodiments, said supporter can stabilize a marker comprising for example a light emitter and/or a gyroscope and/or a magnetometer and/or an accelerometer. Said supporter allow avoiding slip off of said supporter sensor from said supporter. Optionally, by adhesion of said sensor to said supporter.

In some embodiments, the patch 15 is positioned under a garment 10, said garment covers a body of a user 12.

In some embodiments, when the garment 10 is held by the gripping sections 11, a stretched portion of the garment 16 is formed above the marker 13, this un-wrinkled portion reduces noise which arises from layers of wrinkled clothing that covers the LED emitters 14. In some embodiments of the invention, a stretched garment portion reduces scattering of the signal.

Inflatable Pillow:

In some embodiments, the supporter 19 has an inner lumen and an external wall. Optionally, said wall is elastic. In some embodiments, said external wall is made of Polypropylene and/or silicon.

In some embodiments, said inner volume can be modified (e.g., by enlarging said volume or by reducing it). Optionally, said supporter is inflatable.

In some embodiments, said external wall comprises an inflation port, through which gas is inserted into said inner lumen.

Optionally or alternatively, supporter 19 is a balloon.

In some embodiments, the balloon is used to support said marker. Optionally, balloon 19 is positioned in a desired body region. In some embodiments, balloon 19 includes an upper said and a lower side.

Optionally the lower side, faces the body and the upper side faces the marker.

As shown at FIG. 9A, supporter 19 (e.g., balloon) is symmetric.

Optionally, said supporter has two axes, for example a horizontal axis, and a vertical axis which is perpendicular to the horizontal axial. In some embodiments, the horizontal axial and the vertical axial are equal in length.

Optionally or alternatively, the horizontal axial is longer than the vertical axial.

In some embodiments, supporter 19 is stretchable.

Attachment between Pillow and Body/Marker:

In some embodiments, supporter 19 is attached to the marker and/or to the body.

In some embodiments, said attachment is by adhesive layer, positioned either at its lower side and/or at its upper side. For example, the adhesive layer of supporter 19 may comprise a sticker with glue.

Optionally or alternatively, a reusable sticker which allows, for example to remove and re-attach the supporter to the selected body location and/or marker may be used. In some embodiments, aid adhesive materials comprise Acrylate-based materials. In some embodiments, said sticker may contain a combination of adhesive materials.

Referring now to FIG. 9C, the figure shows a schematic representation of a marker positioned onto a supporter 51. Said supporter provides support for the marker and further has a gripping element 52 by which the garment is attached to the supporter.

For example, supporter 51 comprises two concaved sections 52. In some embodiments, the supporter 51 is placed onto a desired body location, and by pressing the garment towards these concaved section 52, attachment of the garment is achieved.

According to some exemplary embodiments, the device is attached directly to a selected body area at 610. In some embodiments, the device is attached after the removal of a sticker cover, for example to expose a region covered with glue.

At 612, in some embodiments, the patch and the marker are covered by a garment worn by a patient. Optionally, the device is attached to the garment, while the patient is already wearing a garment.

At 614, an exemplary patch comprising a marker is attached to a garment, said garment serving as an anchoring element for said motion monitoring device.

In some embodiments, along with attachment of said patch to the garment, said garment is stretched over the patch.

According to some exemplary embodiments, the device is attached to the body and being activated at 616.

In some embodiments, the device is calibrated, for example by collecting baseline signals for a period of a few breaths from a stationary subject.

In some embodiments, the calibration data obtained at a previous time can be used.

In some embodiments, an automatic calibration process is performed.

In some embodiments, calibration process parameters such as reference breathing volumes are obtained, optionally from the marker and/or from the image sensor and transmitted to a computerized unit.

In some embodiments, said calibration is performed by an algorithm which is embedded in said computerized unit.

Exemplary Adhesive—Based Attachment

Referring to FIG. 8A. In some embodiments, the attachment of patch 25 to a user body is performed by adhesive. For example, attachment patch 25 may comprise a sticker with glue.

Optionally or alternatively, said sticker is positioned at the lower side of patch 25 (e.g., as element 26).

Optionally or alternatively, a reusable sticker which allows, for example to remove and re-attach the device to the selected body location may be used.

Optionally or alternatively, an adhesive material is positioned at the interface between the patch 25 and the garment.

In some embodiments, markers are placed adjacent to the body as shown in FIG. 8A. In this embodiment, the marker or sensor are enclosed in a closed pouch (e.g., exemplary pouch B), which is an integral part of the clothing.

Optionally or alternatively, said pouch is hung over the clothing and/or body of a subject.

In some embodiments, said closed pouch may be attached to the body and/or to a garment worn by said subject by adhesive materials and/or by Velcro (hooks).

In some embodiments, the clothing, e.g., exemplary clothing (i), is a baby outfit with a drawstring which runs through the edges of the embedded pouch (ii). The marker can be fit closer and adjacent to the body by fastening with the drawstring from the outside. In some embodiments, said pouch is made from fabric.

In some embodiments, the patch 25 is adhered to the body on its lower side and to the clothing or sheet on its upper side using 2-sided adhesive tape.

In some embodiments, the clothing or covers are placed over the patch and are lightly bound to it by a sticker which is placed on the upper surface of the patch 25.

In some embodiments, the patch 25 can detach from the clothing after significant movement but easily reattaches again when slight pressure is applied. The adhesive may be a hydrogel which can reattach repeatedly without losing much adhesiveness.

In some embodiments, said adhesive materials may contain an adhesive such as commercial adhesive materials which commonly used for, to allow better attachment to a curvature of some body sections.

Optionally or alternatively, said adhesive materials comprise Acrylate-based materials.

In some embodiments, said sticker may contain a combination of adhesive materials.

In some embodiments, said patch 25 is flexibility in order to fit varied body surfaces.

In some embodiments, said patch 25 has a lightweight and comfortable

In some embodiments, said patch 25 has ow profile (thin) but yet rigid enough to hold marker.

In some embodiments, said patch 25 can detach and reattach to clothing several times.

In some embodiments, said patch 25 can detach and reattach to animal blanket/sweater, especially for sedated animals.

In some embodiments, said patch 25 attaching patch 25 to the garment does not damage garment.

In some embodiments, said adhesive materials by which patch 25 is attached to the garment are not too strong in order not to pull skin when clothing is pulled In some embodiments, said adhesive materials hold 24 hours.

In some embodiments, said adhesive materials are water-resistant.

In some embodiments, said adhesive materials and/or said marker and/or said patch have Low price and low cost to manufacture - we use pressure forming technology.

In some embodiments, said adhesive materials and/or said marker and/or said patch are easy to sterilize with gamma ray or Ethylene oxide.

In some embodiments, said adhesive materials and/or said marker and/or said patch utilizes Small amount of material.

In some embodiments, said top surface of marker can also have adhesive on it.

In some embodiments, said patch 25 attaches without clutching marker from the upper side and interfering with led signal.

Optionally or alternatively, said patch includes one or more notches for attachment of one or more ECG electrodes which are adhered to body (see exemplary element 31).

In some embodiments, said patch 25 is made of a flexible thin sheets of polypropylene. Said patch has variable rigidity so that they hold the marker 23 fixed and yet have flexibility on the region next to the body.

Optionally or alternatively, said patch 25 comprises a notch for the ECG electrode so as to lower the cost of the patch and to allow eliminating the need for adhesive materials addition on patch).

In some embodiments, hydrogel serves as adhesive to clothing so that it can be reapplied several times and does not damage garment.

In some embodiments, a snap-in mechanism is used to keep the marker in place. The patch does not obstruct the upper surface of the marker if a light emitter is present in the marker.

In some embodiments, said patch 25 is anti-reflective, so that its upper part will not also reflect light to the IR sensor.

Exemplary Pillow—Based Attachment

Another embodiment of placing the marker adjacent to the body is shown in FIGS. 8B-C.

In some embodiments, a padded pillow and a holder wrist 95 are placed for example between the thorax and a first layer of clothing 92. Optionally the holder is reusable.

In some embodiments, a marker 93 is placed above (visible from outside) the first layer of clothing. In some embodiments, marker 93 connects to (e.g. by snaps and/or by clicks into) the holder 95 wrist.

In some embodiments, the marker 93 optionally includes an electronic circuit that can include: a power source, a single or several motion sensors, optical emitters, a wireless communication device and/or processing units.

Referring to FIG. 8C

An embodiment of a marker 101 and holder 102 are shown together in FIG. 8C, without the garment in between them.

In some embodiments, the marker 101 and holder 102 of figure 8C may include the marker 93 and holder 95 of FIG. 8B.

In some embodiments, the marker 101 optionally lies outside the first layer of clothing and the holder 102 optionally lies under the clothes.

Optionally the clothing and/or a soft backing lies directly adjacent to the thorax.

Referring now to FIG. 9B, the figure shows a schematic representation of a marker positioned between a garment and the body and onto a holder (e.g., a soft interface 110).

In some embodiments, said holder 110 may include an external wall and an inner compartment defined by said external wall. In some embodiments, said inner compartment may include foam. In some embodiments, inner compartment may contain a solid pellet. In some embodiments, said materials may support said marker in a desired position inside said inner compartment.

In some embodiments, said holder may include a marker senor 111. The sensor 111 and/or the holder 110 may optionally lie beneath the clothing.

Optionally or alternatively, the sensor 111 and/or the holder 110 may optionally lie above the clothing.

In some embodiments, a cap 112 (said cap may be for example a plastic ring) may be used to secure the clothing to the holder 110.

In some embodiments, the marker can optionally include a magnet (for example a permanent magnet).

Optionally or alternatively, the marker may include magnetometer (as shown for example in FIGS. 10A-B-11A-B).

In some embodiments, said magnetometer is attached to the side of the bed or to the clothing with a separate holder.

As the body of the subject's (with the magnetometer on top of it) moves in relation to the magnet, which may be positioned on the bed and/or on the body of the patient, it modifies the magnetic field which is in vicinity of marker and thereby allowing measurements of magnetic field changes which can be converted directly to distances, e.g., breathing distances.

Optionally the magnet does not move rigidly with the marker, during breathing. For example, said magnet may be embedded in a hand wrist. In such case, during breathing of the subject, the thorax of the subject moves while the hand does not move. In some embodiments, the marker, that includes a magnetometer therein, moves according to the movements of the thorax and the distance between the magnetometer and the magnet which is placed in said wrist changes.

In some embodiments, said altered distance is detected by said magnetometer, and transmitted to a computerized unit to be analyzed.

Exemplary Breathing Motion Monitoring Methods:

In some embodiments, a variety of sensors can be used to track the chest wall motion such as: an image sensor overlooking the subject, a magnetometer, an accelerometer, a gyroscope, piezo sensor and/or a pressure sensor.

In addition, ECG sensors and/or temperature sensors can be incorporated into the wearable sensor, for example, to provide physiological data.

In some embodiments, said sensors can be incorporated for example in marker 216 (shown in FIG. 3).

Breathing Motion Monitoring which is Based on Light Emitter Location:

In one embodiment, an image sensor (e.g. image sensor 18 shown in FIG. 1) is used that tracks the 3D position of optical emitter (As shown in FIGS. 15A-B), or reflective markers affixed to the subject's thorax can be used to determine respiratory parameters.

In an embodiment, using reflectors, light (e.g., IR light) is transmitted by a source associated with the imager and this light passes through the garment. Said light is reflected back through the garment by such one or more reflective markers, to be imaged by imager 18.

In some embodiments, tracking of said LED's is compared to a reference point.

Said point may be a point in the room and/or a point on the subject's body.

In some embodiments, the image sensor (for example image sensor 18 in FIG. 1) detects the location of the LED and the reference point.

In some embodiments, data from the image sensor is transmitted to a computerized unit and analyzed. In some embodiments, the distance between the moving LED (which moved in accordance with the movements of the thorax) in relation to the reference point changes. These altered distances provide indications regarding the breathing motions of the subject to the computerized unit.

Exemplary Motion Monitoring by Tracking one or more LED's Location

In some embodiments of the invention, a method on how the 3D tracking can be continued even if some of these LEDs are disrupted leaving say only a single LED to track is provided (e.g., as described in flowchart of FIG. 13).

In some embodiments, the breathing axis in 3D (e.g. X, Y and Z axis) space is determined from the tracking of 2 or more LEDs arranged in a known geometric configuration onto said marker.

These axis are fixed in space so long as the motion monitoring device (for example device 210 in FIG. 3) and subject are both stationary.

In some cases, only one LED is visible from a given time onwards. In such case the LED 3D location is determined by evaluation its current location by assessing its 3D position at an earlier time plus a vector 'u' along the direction of the breathing axis.

For example, the length of a vector 'u' can be determined by requiring that a current tracked 2D image position of the LED corresponds to the projection of the earlier 3D LED position plus 'u'.

This method is can be more accurate when the breathing axis makes a larger angle with the axis from the camera center to the LED in question. This may guide positioning of imager 18 and/or the marker 13 (for example in FIG. 1).

Asides from the degenerate case where the 2 axes coincide, in some embodiments, the respiratory parameters can be determined from a single optical emitter (e.g., signal emitter 214 in FIG. 3) as long as the position of the subject relative to the camera (e.g., image sensor 18 in FIG. 1) has not changed relative to the time when two or more emitters were visible in the image sensor, for example, emitter positioned onto said marker 216.

Breathing motion monitoring which is based on inertial sensors:

Accelerometer and/or Gyroscope:

In some embodiments, motion of a subject's body is monitored by analyzing data received from inertial sensors, for example, an accelerometer, and/or a gyroscope.

In some embodiments, said inertial sensors are positioned adjacent to the subject's body and sense acceleration and/or tilts of the body of the subject.

In some cases, for example during breathing, the thorax of the subject's moves and the monitored movements are depicted by the sensors and transmitted to a computerized unit for analysis.

The acceleration vector oscillates over time due to the linear component of the marker motion and also due to the rotation component. The time-dependence of the rotation angle over time represents the breathing signal which can be analyzed to determine respiratory parameters such as respiratory rate.

In some embodiments, an accelerometer is placed on the chest wall and it provides a 3-axis acceleration signal in a body coordinate frame.

Optionally or alternatively, a gyroscope is placed on the chest wall and it provides a 3-axis orientation and/or angular velocity signal in a body coordinate frame.

In some embodiments, the accelerometer measurements themselves can be filtered to produce a breathing signal. The breathing signal can be analyzed to obtain respiratory rate and "no-breath" epochs. Relative volume can be calculated by comparing amplitudes to a baseline signal.

In some embodiments of the invention, the monitoring method relies on knowledge of the approximate breathing axis in body coordinates which is perpendicular to the chest wall.

The breathing motion of a point on the chest wall is only approximately linear and possesses a "banana" shape with a small curvature (often less than a degree).

The accelerometer readings are affected by the device rotation.

For example, a subject in the supine position: such subject breaths along an axis close to the gravity axis. The changes of the acceleration measurements perpendicular to this axis are mainly due to the curvature of the breathing axis rather than the acceleration due to motion.

In some embodiments, filtering particular components of the accelerometer signal by digital filters, produces an oscillating breathing signal whose frequency is the respiratory rate.

In some embodiments, the amplitude of the motion component of the acceleration along the breathing axis can be compared to a baseline value to calculate relative volume.

In some embodiments, the motion component of the acceleration along the breathing axis can be further integrated twice to find the breathing amplitude in length units.

Accelerometer+Light Detection

In some embodiments of the invention relates to monitoring body motions of a subject by tracking signals received from at least one motion sensor (e.g., an inertial sensor) and at least one light emitter.

In some embodiments, said motion sensor and said light emitter are positioned onto the body of a subject and move along with the movements of the body.

In some embodiments, the acquired data received from said sensors is analyzed by a computerized algorithm. In some embodiments, the analysis is based on data received both from the motion sensor and from the light emitter. The sensors are analyzed to determine non-breathing motion epochs by means of the magnitude of the breathing signal and also by determining whether the movement is unidirectional. For epochs where the motion is mainly breathing motion, the sensors are used to extract a signal representative of breathing and to extract from it respiratory parameters.

In some embodiments, said detected motions are movements of a subject's thorax. In some cases, such movements may be small and hard to detect and therefore each of said sensors may compensate the sensing limitations of the other.

The inertial sensor acquired measurements of breathing motion can be combined with the location analysis of the LED location to provide improved estimates of the respiratory motion.

The accelerometer analysis can provide a complementary independent view: in that it provides information regarding the curvature of the essentially 1-D breathing translational movements. Combining the signals to calculate respiratory parameters enables more accurate estimation of respiratory parameters by combining independent aspects of the respiratory motion.

In on example, inertial or other sensing is used to provide data on movement along the breathing axis. Optionally or additionally, such inertial or other sensing is used to detect movements due to non-breathing movement. Optionally or additionally, one type of sensing is used as backup when data from the other type of sensing is missing and/or noisy. Optionally or additionally, providing two types of sensing allows one measurement to act as a baseline correction (e.g., against signal drift) of the other sensing modality). Optionally or additionally, the two data signals are combined, so as to reduce the average effect of noise and/or to assist in coherent detection at times when a breathing signal is expected and/or indicated by one of the sensing modalities.

In some embodiments, due to low sampling rates, drift errors can easily be introduced. There are several ways this limitation can be overcome. One way is to use a baseline session where several breaths are recorded at normal tidal breathing. The deviations of breath amplitudes to the baseline breaths can provide a measure of relative amplitudes or more generally relative volumes.

In some embodiments, a combination of an accelerometer and an imaging sensor can also be used to overcome some accuracy limitations.

The determination of 3D breathing amplitudes can be deduced from the acceleration amplitudes using a learning period in which signals from both sensors are available for calibration.

Furthermore, a single LED can be used to deduce 3D amplitudes by using the inclination of the accelerometer relative to gravity and related directions deduced from the image such as the vanishing point of vertical lines in the image.

Magnetometer:

In some embodiments, a magnetometer sensor can also be used to assess 3D movements of a subject thorax.

In some embodiments, said detection is detection of 3D distances by introducing a magnet near the sensor.

In some embodiments, said magnet is positioned on a subject's body. Optionally or alternatively, said magnet is positioned in the room, near the subject.

In some embodiments, the magnet and the marker (which includes a magnetometer therein) are not rigidly connected to each other.

In this manner, the distance between them varies due to breathing motion (e.g., the magnet and/or sensor move due to breathing). The frequency of the magnetometer signal is the respiratory rate; the 3D amplitude can also be deduced by modelling the magnetic field of the magnet in its vicinity and correcting for the earth's magnetic field. Deducing 3D amplitudes relative to a baseline value, requires a less detailed modelling of the magnetic field.

Referring now to FIGS. 10 A-B.

The figures exemplify an assembly of a marker and a magnet, both positioned for example on a diaper.

In some embodiments, the marker is positioned in proximity to the magnet.

The marker includes a magnetometer therein (see for example element 234 in FIG. 3). In some embodiments, the magnet is held by a holding strep near the marker. In some embodiments, said magnet generates a magnetic field which is detected by the magnetometer.

As the body of the subject (e.g., a baby) moves due to the breathing movements, the distance between the magnetometer and the magnet changes, resulting in a variation in the magnetic field at the magnetometer. The variation is dependent on the relative change in distance between magnetometer and magnet which can be of the order of a few mm.

In some embodiments, said magnet can be attached to bed and /or to a wheelchair.

Optionally or alternatively, said magnet is attached to said marker and said magnetometer is placed on a bed.

In some embodiments of the invention, said marker may include a magnetometer and said body motions may be monitored without a light emitter.

Referring now to FIGS. 11A-B. The figure shows an exemplary embodiment of a marker positioned on the stomach of a baby and a magnet positioned in a wrist.

In such case, during breathing of the subject, the thorax of the subject moves while the hand does not move. In some embodiments, the marker, that includes a magnetometer therein, moves according to the movements of the thorax and the distance between the magnetometer and the magnet which is placed in said wrist changes.

In some embodiments, said altered distance is detected by said magnetometer, and transmitted to a computerized unit to be analyzed.

FIGS. 12 and 13 are two exemplary flowcharts of the analysis process.

FIG. 12 describes a use of four or more rigidly arranged markers on a planar plate, e.g., a marker for the transmission of motions of a patient to an image sensor.

FIG. 13 describes an exemplary analysis process with a use of one or more rigidly arranged markers on a planar plate, said marker is used for monitoring breathing motions, respiratory rate and relative volume of a subject with a limited amount of non-breathing motion data (e.g., obstructed LED's).

Methods as described herein may use algorithms and hardware as described in the previous PCT Application No. PCT/IL2017/050466.

Before describing the steps of the flowcharts, some exemplary system considerations are described herein below:

In some embodiments, there are special considerations for monitoring subjects for long periods, specifically children and/or in cases when the system is used in a home-like environment.

To address these considerations the system, at some embodiments, can be designed with the following features and adjustments:

In some embodiments, the motion monitoring system may include a use of a washable sensors. For example, said sensors may be placed in a waterproof environment, for example by enclosing it with epoxy.

In some embodiments, the motion monitoring system may include a use of power source. For example, said power source may include a use of a rechargeable battery with wireless recharging through the epoxy enclosure.

In some embodiments, the motion monitoring system may include a use of a microcontroller included in the sensor circuit-board. In some embodiments, a Wireless communication is turned on only for short times when needed, e.g. when there is an alert to allow reduction of emitted radiation.

In some embodiments, the motion monitoring system may include a use of a limited computational resources. For example, such limitation may be achieved by incorporation a processing unit on the body of the markers. Optionally, such unit may be used to process physiological signals and compress them for transmission and/or extract data, such as temperature passing a threshold or converting ECG to heart rate and/or other ECG attributes.

In some embodiments, said unit can be minimized by calculating only relative parameters and by using the image sensor which performs computations on-board DSP.

In some embodiments, the system may include activating alerts that can be immediate and audible be initiated. For example by including a speaker in the sensor circuit.

In some embodiments, the system may provide a summary of the sessions. For example such summary may be displayed for the user at the end of a session (e.g., at night of sleep) a summary of all out of the ordinary events can be displayed to the user.

Referring now to flowchart of FIG. 12. The figure shows an exemplary flowchart of the analysis process which relies on 3 or 4 or more rigidly arranged markers on a plane, e.g., on planar plate (e.g., a marker upper flat face).

In some embodiments, at 101 the motion monitoring process begins by obtaining 2D tracking locations of markers, while said markers are placed onto said patch and being attached to a garment.

In some embodiments, at 102, the location of the plate in relation to the camera's (e.g., an image sensor) frame of reference (origin at camera lens) is determined by using the marker's known geometrical arrangement on the plate.

In some embodiments, at 103, the distance between the current location of the marker plane and a reference parallel plane is calculated.

In some embodiments, by considering the relative placement of consecutive planes (above or below), a 1-dimensional signal representing the signed 3D distance is displayed, as shown at 104.

In some embodiments, at 105, the signal is analyzed for features such as one or more of peaks, troughs and/or amplitudes.

In some embodiments, at step 106, the respiratory rate, phase delay and/or the relative volume are calculated from the 1D signals in a prescribed time epoch, after which the process may restart at 101.

Referring now to flowchart of FIG. 13. The figure shows an exemplary flowchart of the analysis process which relies on one or more rigidly arranged markers on a planar plate (e.g., a marker upper flat face) during breathing motion with a limited amount of non-breathing motion signals.

In some embodiments the process begins by detecting the 2D locations of the markers in the image frame, as shown at 201.

In some embodiments, at 202, the location of the plate in the camera frame of reference is determined assuming the plate remains parallel to its position in previous frames of the breathing motion, or by using data from another sensor. It is noted that the method of FIG. 12 may be interleaved with the method of FIG. 13, for example, making this assumption about the plane when fewer than 3 or 4 LEDs are imaged.

In some embodiments, at 203, the distance between the current plane and a reference parallel plane is calculated. In some embodiments, by considering the relative placement of consecutive planes (above or below), a 1-dimensional signal representing the signed 3D distance is displayed, as shown at 204.

In some embodiments, at 205, the signal is analyzed for features such as peaks, troughs, and amplitudes.

In some embodiments, at 206, the respiratory rate, phase delay and the relative volume are calculated from the 1D signals in a prescribed time epoch, after which the process restarts at step 201.

Exemplary Device Connectivity

According to some exemplary embodiments, the motion monitoring device receives and/or transmits wireless signals to one or more remote devices.

Reference is now made to FIG. 14A depicting the connectivity of a device, for example device 131 attached to the garment 132 of a subject 130, according to some exemplary embodiments of the invention.

According to some exemplary embodiments, device 131 communicates by wireless signals, for example Bluetooth and/or WiFi signals with a remote device 133.

In some embodiments, the remote device 133 communicates with a wearable device, for example a smartwatch or a bracelet.

Alternatively or additionally, the device 133 communicates with a mobile device 140, for example a smartphone or any other mobile device.

In some embodiments, a software application or a software program installed in a memory of the wearable device 131 and/or in the mobile device 140 and/or in the remote device 133 and controls and/or monitors the operation of the device 131.

In some embodiments, the software application or the software program allows to modify at least one parameter of the delivered signal, for example intensity, voltage, frequency, pulse width.

According to some exemplary embodiments, the remote device 133 is in communication with an information storage cloud, for example cloud 310 by a wireless signal. In some embodiments, a processed data and/or control commands can be transmitted one way between:

The marker and the computerized unit, for example signals generated by the magnetometer may be transmitted to the computerized unit.

The marker and the information storage cloud, for example signals generated by the magnetometer may be transmitted to the storage cloud, and for example, data can be transmitted from the computerized unit to the information cloud, for example breathing motion parameters analyzed by said computerized unit.

In some embodiments, a processed data and/or control commands can be transmitted tow way between:

The marker and the computerized unit, for example signals generated by the magnetometer may be transmitted to the computerized unit.

The marker and the information storage cloud, for example signals generated by the magnetometer may be transmitted to the storage cloud, and for example, data can be transmitted from the computerized unit to the information cloud, for example breathing motion parameters analyzed by said computerized unit.

In some embodiments, the device 133 and/or in the mobile device 140 and/or device 131 transmits to the cloud 310 or mobile device 140 data and/or measured values of at least one physiological parameter, for example breathing volumes.

Optionally, the cloud includes a processor with at least one table and/or at least one algorithm that modifies at least one parameter of the delivered signal based on the information received from the device 133. For example, such modification can include calculating a positon based on image data, trend of breathing amplitudes and "no breath" episodes over the last nights.

In some embodiments, the cloud 310 then delivers the modified parameter values to the device 133.

In some embodiments, software applications or programs installed in the wearable device 131 and/or the mobile device 140 comprise at least one table and/or at least one algorithm. In some embodiments, the wearable device 131 and/or the mobile device 140 modify values of at least one signal parameter values based on the information received from the device 133.

Reference is now made to FIG. 15A. The figure shows an exemplary embodiment of four light emitters positioned under an unfolded (wrinkle-free garment). According to the figure, when the garment is not folded, a blurry shape of the light is formed.

Reference is now made to FIG. 15B. The figure shows an exemplary embodiment of four light emitters positioned under a wrinkled garment. According to the figure, as the light passes through a wrinkled garment the light is scattered, and/or undergoes refractions and/or reflections and as a result, a blurrier shape of the light is formed.

In some embodiments of the invention, a local processor (e.g., in the imager) processes such images to detect blobs of lights and estimate the center (and/or other fixed geometrical reference property) of such blobs. Coordinates of these centers are used for determining 1D, 2D or 3D movement and/or movement type, for example, as described herein. The 3D distances are used to calculated breathing parameters. A local processor on the marker analyzes the motion sensor and calculates the breathing signal (e.g. rotation angles) which are in turn used to calculate respiratory parameters.

Exemplary Activation of the Device by a User

Reference is now made to FIG. 16A depicting a process of using the device (for example device 210 in FIG. 3) by a user, according to some exemplary embodiments of the invention.

According to some exemplary embodiments, the user activates the device, at 1604. In some embodiments, the device is activated by pressing a power switch of the marker, for example marker 210 shown in FIG. 3.

Optionally or alternatively, removal of an insulator between at least one battery, for example battery 222 and a different part of the circuitry of marker 210, shifts the power/activating mode of the marker to a stand-by mode.

In some embodiments, the power switch or button switches the power mode between OFF, Standby and ON. Optionally, the power switch or button is mechanical, magnetic or an isolation tab which exposes contacts and close circuit when removed.

According to some exemplary embodiments, a software application (app) installed in a mobile device and/or in a remote unit and/or in the wearable device is activated at 1606. It can be activated from a mobile application or from the base station or from a switch on the marker.

In some embodiments, a user couples the wearable device with a smartphone and/or with a remote control unit at 1608.

In some embodiments, the wearable device is coupled with smartphone only after an identification process is completed. In some embodiments, to prevent unauthorized coupling, an identification process, which optionally comprises insertion of a password to allow coupling, is performed.

According to some exemplary embodiments, the device is applied to the desired body area at 1610.

In some embodiments, the device is applied to the selected body area by exposing at least one adhesive tape located on the device patch, and attaching the at least one adhesive tape to the skin.

In some embodiments of the invention, the device is applied to a selected body area onto a supporting element, for example a pillow which is positioned between the body and the device. In some embodiments, the device is being attached to the garment, by an attachment, as shown for example at FIGS. 7A and 7B element 11.

Optionally or alternatively, the device is positioned on the monitored body area of the body, relatively to a magnet, as shown for example at FIG. 10B, for example by a bent that holds both the marker and the magnet in desired body areas.

According to some exemplary embodiments, motion monitoring is activated at 1612.

In some embodiments, said activation may include move device from standby mode and from OFF mode to an ON mode. Said activation may include turning ON a light emitter and/or a motion sensor and/or a magnetometer.

According to some exemplary embodiments, the sensors (e.g., the inertial sensors and/or the magnetometer) and/or the light emitting LED's are activated at 1612.

In some embodiments, the monitoring motion sensors (e.g., for sensing breathing motions) are activated using the software program installed in the mobile device which is paired to the wearable device, for example the smartphone and/or tablet and/or remote unit.

According to some exemplary embodiments, usage information and/or data are uploaded, optionally automatically, to a cloud based storage, for example cloud 310 shown in FIG. 14A, at 1614.

Alternatively or additionally, the usage information and/or data are stored in the writable readable memory, for example memory 220 shown in FIG. 3 of the device.

In some embodiments, the usage information and/or data are stored in a memory of an external device, for example mobile device shown in FIG. 14A.

Referring to FIG. 16B and FIG. 16C. The figures show an exemplary user interface displays, optionally presented as a software application (app) installed in a mobile device, for example a smartphone.

Visualization:

The figure shows a snapshot of a display of relative volume ratios shown on a user interface.

In some embodiments, a user interface may include data regarding the respiratory rate of a subject.

Optionally or alternatively, the interface may include data regarding the tidal volume ration of a subject.

In some embodiments, for determining the chest wall displacements a visualization of these movements can be displayed on a user interface as shown in FIGS. 16B-C.

In some embodiments, this visualization has as its basis a physiological model of muscle movements, for example the inflating chest movements are mainly associated with contraction of the intercostal muscles (as shown in FIG. 16C); The inflating abdomen movements are mainly associated with contraction of the diaphragm and its downward movement which causes abdomen inflation.

Additionally, the user interface may include parameters regarding the system and marker operation status.

In some embodiments, more than one marker may be used. For example one marker may be positioned onto the chest area and another marker which may be placed for example onto the abdomen area.

In some embodiments, one marker may detect body motion movements such as coughing movements.

In some embodiments, one marker may detect body motion movements such as coughing movements.

In some embodiments, said detected body motions, said detected system operation status parameters, and marker operation status parameters may be transmitted to a computerized unit and/or to a user display interface.

As such, the user interface display may present the status of each of the markers in combination and/or separately.

Reference is now made to FIG. 17.

The figure shows an exemplary graph representing image processing results of a light emitter attached to the garment and supported by a supporter (e.g., a supporting pillow)—marked as solid line and a light emitter attached to the garment while not being supported by a supporter—marked as dotted line.

X axis represents time and Y axis represents the distance between the light emitter and the image sensor.

As the pillow stabilizes the light emitter to the body, a correlative distance of the light emitter, image sensor, and body is preserved.

Reference is now made to FIG. 18.

The figure shows a configuration of the magnet, marked as a circle positioned at an exemplary distance of 5cm from a marker.

According to an exemplary embodiment, a magnetometer is positioned inside the marker. Both marker (and magnetometer) and magnet are not-rigidly attached (the movement of the magnet is not effected by the movement of the magnetometer) and positioned on the patient's body.

Right figure illustrates the location of the marker and magnetometer relatively to the magnet.

Left figure shows an exemplary magnetometer signals of X, Y and Z axis.

When the amplitude of the magnitude decreases, the distance between the magnet and the magnetometer increases as a result of a decreased influence of magnetic field on the magnetometer and vice versa.

Reference is now made to FIG. 19A the figure shows an IR sensor imaging analysis. This signal is obtained from a single marker with one or more LEDs.

The IR signal is represented in 2D by pixels of the image sensor. The amplitude represents a distance in the image between the location of the light emitter at different times during breathing.

As the thorax of a patient moves during breathing, so moves the location of the light emitter which is positioned onto the thorax of the patients. During such movements, the distance between the reference point and the light emitter location changes. The altered distance is represented by the motion amplitude.

Reference is now made to FIG. 19B the figure shows a spirometer analysis. The graph represents the breathing volume of a patient. High points represent the end of inhalation stage, and low point represents the end of exhalation stage. As can be seen, there is a good correlation between the IR signal and the Spirograph signal. Optionally, the Spirograph signal is used to calibrate the IR signal processing (e.g., to generate a translation table or function mapping movements or light positions to tidal volume).

Reference is now made to FIG. 19C the figure shows a magnetometer analysis. The graph represents the breathing volume of a patient. High points represent the end of inhalation stage, and low point represents the end of exhalation stage. As can be seen, there is a good correlation between the IR signal and the magnetic signal. Optionally, the IR signal is used to calibrate the magnetic signal (e.g., to generate a translation table or function mapping movements or light positions to tidal volume).

Further Exemplary Monitored Data by the Monitoring System:

Relative Volume:

In some embodiments, relative breathing motions are monitored. For example, said relative breathing motions are the movements of the thorax of a subject pre-sedative state and during sedative state. This may be in addition to or instead of breath-to breath detection of relative change. For example, this may include comparing breathing between two times that are at least 3 minutes or at least 10 minutes apart.

In some embodiments, prior sedative, the motions of the thorax of a subject are monitored, optionally using the light emitter. Optionally or alternatively, using accelerometer.

In some embodiments, during sedative state, the thorax movements are monitored also by using the same sensors, and compared.

Heart Rate:

In some embodiments, heart rate of a subject is monitored. In some embodiments, such monitoring uses data acquired while the patient is not inhaling or exhaling to a significant extent. When the subject is not moving his thorax due to breathing, movements of the thorax are attributed to the heart beats. In some embodiments, these minor movements are monitored, optionally by detecting and analyzing the location of at least one light emitter. In some embodiments of the invention, non-breathing time windows are detected by analyzing the breathing waveform and identifying times that are after exhalation and before inhalation.

Visualization:

In some embodiments, visualization of the movements of the chest wall displacements is performed, optionally by allowing displaying of these movements to a user and/or to a caregiver.

This visualization optionally has as its basis a physiological model of muscle movements: the inflating chest movements are mainly associated with contraction of the intercostal muscles; the inflating abdomen movements are mainly associated with contraction of the diaphragm and its downward movement which causes abdomen inflation.

Identifying Breathing Parameters & Alerts:

Learning Schemes:

In some embodiments of the invention, it is desired to determine deterioration in breathing in order to provide immediate alerts. One way of doing this is by tracking respiratory parameters such as respiratory rate, tidal volume, respiration volume, respiration rate, minute ventilation, and/or stoppages of breath and alerting accordingly.

In some embodiments, these can be found by analyzing accelerometer signals from the marker and/or the magnetometer signals and/or an optical position signals.

In some embodiments, for example, analysis may include one or more or even all of the following:

1. Combine 3-axis signals of the accelerometer or the 3-axis signals of the magnetometer and/or the 3D position measurements into a single signal which emphasizes the variations due to breathing.

This can be achieved for example by projecting the acceleration vector onto the body direction which has the largest variation in acceleration values or projecting the position measurements onto the 3D breathing axis.

2. Filter the resulting 1D signal to reduce noise, for example high frequency measurement noise and/or other sources of motion (heartbeat for example).

3. Identify epochs of extensive non-breathing motion where respiratory parameters cannot be extracted and/or the subject is very active and/or moving around. For example, this may involve identifying transitions from breathing motion to extensive non-breathing motion by identifying say 1-3 second intervals whose signal features are much different than that in breathing motion.

The signal features that may be used include for example: signal amplitude relative to recent typical breathing amplitude, signal derivatives relative to recent breathing derivatives, Fourier transform amplitudes in the breathing and extensive non-breathing motion regimes, etc.

These features may also be used to develop (for example training an artificial intelligence (AI) routine) a classifier and/or determine thresholds based on labelled data. For example the data may include transition between breathing and extensive non-breathing motion. Decision trees or random forests classifiers may be used.

4. A classifier for identifying transitions from extensive non-breathing motion back to breathing motion may also be developed. Optionally the time intervals for developing this classification may be slightly longer, say 5-8 seconds. Preferably the breathing features calculated and shown to the user should be accurate. In some cases, during epochs of extensive non-breathing motion, respiratory parameters are not calculated.

5. During the breathing motion epochs the signal is optionally analyzed for respiratory parameters such as respiratory rate and amplitudes. Analysis may use Fourier domain and/or time domain methods. Relative minute ventilation and tidal volume respiration volume, and/or respiration rate, may be found by comparing amplitudes of the signal to baseline signals of the subject in question.

6. During the breathing motion, epochs of No-Breath are optionally identified. For example no-breath may be identified by classifying segments of 15 or more seconds based on features for example one or more of: goodness of fit to a low-order polynomial curve to time segments which are optionally filtered in various ways. For example, the time segments may be high passed filtered before fitting to a low order polynomial curve.

Based on collected data of apnea performed in the lab, thresholds are set to reduce false alarm rate for apnea. For example, the goodness of fit analysis can be carried out for overlapping time intervals, say each of length 15 seconds overlapping by 5-10 seconds.

7. Alerts: Alerts are optionally sent whenever thresholds are crossed such as for example respiratory rate below a threshold, apnea for longer than a duration episode and minute ventilation much below the baseline value. Alerts may be based on other classification schemes.

8. Wake-up action: In some embodiments, on the marker circuit it is possible to activate a wake up alarm, for example a vibrating motor to attempt to wake up the subject. For example a wake up alarm may be triggered once a No-breath alert occurs.

Improved Accuracy Based on Simulated Data:

In accordance with some embodiments of the invention, use is made of that displacement of the chest wall is correlated with the tidal and/or respiratory volume. However, the relation between accelerometer readings and volume are optionally programmed. For example, one possibility includes integrating motion sensor measurements over time to deduce displacement. The results may be corrected for drift due to the level of accelerometer measurement noise. Alternatively or additionally, a regression model may be developed between accelerometer time signals of a breath and tidal and/or respiratory volume (for example using AI). For such a goal, a large amount of training data is optionally collected. In some embodiments, the monitoring system may not be equipped with an optical sensor. Optionally another means may be supplied for measuring tidal and/or respiratory volume and/or displacement.

In some embodiments, a database of breaths is created which includes for example 3D displacement measurements and/or accelerometer measurements. For example, this may be performed a priori using a camera (e.g., image sensor 18) and/or motion sensors to collect labelled data on a training set of a subject.

In some embodiments, accelerometer measurements may be variable and/or noisy and/or are dependent on the exact subject pose. Optionally, simulations of accelerometer measurements that correspond to a large number of breaths including repetitions of identical breaths are used in order to interpret the data set. Alternatively or additionally 3D breathing data may be obtained from some subjects and/or used as a basis for planning a robot's arm motion to replicate the 3D breathing motion.

A motion sensor is optionally being attached to the robot's arm and/or measurements of the accelerometer signal can be obtained by rerunning the robot and adding variations to the robot motion such as changes to the inclination angle of the marker to gravity, changes to the breathing 3D trajectory such as scale changes of amplitude and time.

Once a large amount of trajectory data has been collected, a model is optionally developed (for example using AI).

The model optionally maps accelerometer trajectories to overall displacement of a breath and/or to relative volume. A regression model can be developed for example using neural networks and/or other machine learning techniques. The model may be applied to the accelerometer measurements without the need for displacement measurements.

The estimates of volume are optionally made in real time in some embodiments. The above method can be implemented with either accelerometer measurements and/or can be replaced or augmented by the gyroscope and/or magnetometer measurements.

In some embodiments, a robot simulator may be used to simulate additional scenarios from the base optical position data. For example, non-breathing motion disturbances can be added to the breathing motion. These non-breathing motion disturbances may be simulated and/or may be taken from optical recordings of subjects.

For example, measurements may be made while the subject performs different kinds of movements such as head and neck movements, tremor, slight sliding in bed, change of the relative location of the marker to the chest, and so on. New scenarios of chest movements can be composed and simulated by the robot, by combining several measured optical scenarios to occur in unison. The multitude of scenarios are optionally used to augment the collected data to a large database for which machine learning models can be utilized such as CNN's and RNN's to deduce respiratory parameters from real time accelerometer data.

The learning scheme is optionally personalized to a subject. For example, personalization may include adjusting the training scenarios to match the possible scenarios and/or frequency thereof of the subject in question. For example, the range of breathing frequencies and amplitudes of breathing in the training set may be scaled to the range expected for the subject based on defaults based on age, weight and/or BMI.

It is expected that during the life of a patent maturing from this application many relevant motion monitoring systems will be developed; the scope of the term motion monitoring is intended to include all such new technologies a priori.

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A motion monitoring system including a wearable motion monitoring device comprising:
   a first marker positionable onto a thoracic area of a subject, said first marker comprising:
   a first marker housing
   a first electronic circuitry unit configured to move with said first marker housing;
   at least one first motion sensor including a first accelerometer configured to detect at least one body movement and configured to transmit first signals indicative of the at least one body movement to said first electronic circuitry, said first signals transmitted by said at least one first motion sensor including a first rotational component of the at least one body movement, said first electronic circuitry configured to transmit said first signals received from said at least one first motion sensor;
   a first patch sized and shaped to be positioned between a thoracic body region of the subject and said first marker housing, said first patch configured to hold said first marker and comprising:
   a first flexible patch body; and
   a first holder to hold said first marker housing;
   wherein said first patch is sized and shaped to be applied to the thoracic body region of the subject;
   control circuitry configured to receive said transmitted first signals from said first electronic circuitry;
   a second marker positionable onto an abdominal area of the subject, said second marker comprising:
   a second marker housing;
   a second electronic circuitry unit configured to move with said second marker housing;
   at least one second motion sensor including a second accelerometer configured to detect at least one body movement and configured to transmit second signals indicative of the at least one body movement to said second electronic circuitry, said second signals transmitted by said at least one second sensor including a second rotational component of the at least one body movement, said second electronic circuitry configured to transmit said second signals received from said at least one second motion sensor;
   a second patch sized and shaped to be positioned between an abdominal body region of the subject and said second marker housing, said second patch configured to hold said second marker and comprising:
   a second flexible patch body; and
   a second holder to hold said second marker housing;
   wherein said second patch is sized and shaped to be applied to the abdominal body region of the subject;
   wherein said control circuitry is configured to receive said transmitted second signals from said second electronic circuitry, to combine said received first and second signals from said respective first and second electronic circuitries, said combined signals including the first and second rotational components of the thoracic and abdominal body regions, respectively, into a single signal which emphasizes variations due to breathing between the thoracic area and the abdominal area, and to analyze said combined signals to extract one or more respiratory parameters.

2. The system of claim 1, wherein each of said first holder and said second holder has a flexible body and has variable rigidity.

3. The system of claim 2, wherein each of said first and second patch is formed from flexible thin sheets of polypropylene.

4. The system of claim 1, wherein each of said first marker housing and said second marker housing includes an upper face of said respective flexible patch body, and a lower face of said respective flexible patch body, wherein one or more of:
   a distance between said upper face and said lower face is between 1 mm and 10 mm;
   a thickness of each said marker is between 1 and 7 mm; and
   a maximal distance between edges of each said marker is 10 cm.

5. The system of claim 1, wherein said first marker is configured to sense inflating thoracic movements associated with contraction of intercostal muscles of the subject and said second marker is configured to sense inflating abdominal movements associated with contraction of a diaphragm of the subject.

6. The system of claim 1, wherein each said patch includes an external wall defining an inner compartment, wherein each of said first marker housing and said second marker housing is held within said respective inner compartment.

7. The system of claim 1, wherein each of said at least one first motion sensor of said first marker and said at least one second motion sensor of said second marker comprises a gyroscope and the accelerometer,
wherein said at least one first motion sensor of said first marker measures at least one of: an orientation of said thoracic body region, an angular velocity of the movements of said thoracic body region, and an acceleration of the movement of said thoracic body region;
wherein said at least one second motion sensor of said second marker measures at least one of an orientation of said abdominal body region, an angular velocity of the movements of the abdominal body region, and an acceleration of the movement of said abdominal body region.

8. The system of claim 1, wherein said at least one motion sensor of each of said first and second markers comprises a magnetometer which allows measurements of magnetic field changes in a vicinity of the respective marker.

9. The system of claim 1, comprising a transmitter configured to transmit measurements of said first and second motion sensors.

10. The system of claim 1, comprising at least one light emitter, wherein said at least one light emitter is positioned to emit light indicative of displacements of at least one of said thoracic body region and the abdominal body region.

11. The system of claim 1, wherein said system is configured to determine at least one of: a respiratory parameter and an ECG attribute of the subject.

12. The system of claim 11, wherein said system senses a difference in movement of said first marker and said second marker, wherein the difference in movement of said first marker and said second marker is a time delay between movements of said first marker and said second marker, and wherein said system is configured to determine a phase delay from the difference in movement of said first and second markers.

13. The system of claim 12, comprising, for each of said first and second markers:
one or more garment holders to hold a garment worn by the subject in a position overlying said respective marker, wherein said one or more garment holders hold the garment from one side of the garment, and wherein said device includes at least two said garment holders, positioned at a periphery of said wearable motion monitoring device at opposite sides of the periphery, such that a portion of said garment held by said at least two holders can be stretched between the said at least two holders.

14. The system of claim 1, wherein said control circuitry is configured to analyze said combined signals including a time dependence over time of said first and second rotational components to determine said one or more respiratory parameters.

15. The system of claim 1, wherein said at least one first motion sensor of said first marker and said at least one second motion sensor of said second marker comprise only the first and second accelerometers, respectively.

16. The system of claim 15, wherein said first accelerometer of said at least one first motion sensor of said first marker measures at least one of: the orientation of said thoracic body region and an acceleration of the movement of said thoracic body region; and
wherein said second accelerometer of said at least one second motion sensor of said second marker measures at least one of: an orientation of said abdominal body region and an acceleration of the movement of said abdominal body region.

17. The system of claim 1, wherein said respiratory parameters include at least one of:
a tidal volume of the subject; and
a relative breathing volume, wherein a breathing volume at a first time is compared with a breathing volume at a second time that is from 3-10 minutes later than the first time.

18. A motion monitoring system comprising:
a first electronic circuitry unit;
at least one first motion sensor including a first accelerometer positionable onto a thoracic area of a subject and configured to detect at least one body movement and configured to transmit first signals indicative of the at least one body movement to said first electronic circuitry unit, said first signals including a first rotational component, said first electronic circuitry unit configured to transmit said first signals received from said at least one first motion sensor;
a second electronic circuitry unit;
at least one second motion sensor including a second accelerometer positionable onto an abdominal area of the subject and configured to detect at least one body movement and configured to transmit second signals indicative of the at least one body movement to said second electronic circuitry unit, said second signals including a second rotational component, said second electronic circuitry unit configured to transmit said second signals received from said at least one second motion sensor; and
control circuitry configured to receive said transmitted first and second signals including said first and second rotational components, respectively, from said first and second electronic circuitry units, respectively, to combine said received first and second signals from said first and second electronic circuitries, respectively, into a single signal which emphasizes variations due to breathing between the thoracic area and the abdominal area, and to analyze said combined signals to extract one or more respiratory parameters.

* * * * *